(12) United States Patent
Eissenstat et al.

(10) Patent No.: US 7,807,845 B2
(45) Date of Patent: Oct. 5, 2010

(54) RESISTANCE-REPELLENT RETROVIRAL PROTEASE INHIBITORS

(75) Inventors: Michael Eissenstat, Frederick, MD (US); Tatiana Guerassina, Frederick, MD (US)

(73) Assignee: Sequoia Pharmaceuticals, Inc., Gaithersburg, MD (US)

( * ) Notice: Subject to any disclaimer, the term of this patent is extended or adjusted under 35 U.S.C. 154(b) by 519 days.

(21) Appl. No.: 11/077,135

(22) Filed: Mar. 11, 2005

(65) Prior Publication Data

US 2005/0209301 A1    Sep. 22, 2005

Related U.S. Application Data

(60) Provisional application No. 60/552,643, filed on Mar. 11, 2004.

(51) Int. Cl.
*C07D 405/12* (2006.01)
*A61K 31/49* (2006.01)

(52) U.S. Cl. .................................. 548/454; 514/414

(58) Field of Classification Search ............... 548/454; 514/414
See application file for complete search history.

(56) References Cited

U.S. PATENT DOCUMENTS

| | | | |
|---|---|---|---|
| 5,475,027 A | 12/1995 | Talley et al. | |
| 5,502,060 A | 3/1996 | Thompson et al. | |
| 5,703,076 A | 12/1997 | Talley et al. | |
| 5,728,718 A | 3/1998 | Randad et al. | |
| 6,319,946 B1 | 11/2001 | Hale et al. | |
| 6,649,651 B1 | 11/2003 | Wigerinck et al. | |
| 7,087,373 B2 | 8/2006 | Xie et al. | |
| 7,109,230 B2 * | 9/2006 | Erickson et al. | 514/412 |
| 7,157,495 B2 | 1/2007 | Wang et al. | |
| 7,199,148 B2 * | 4/2007 | Tahri et al. | 514/414 |
| 7,285,566 B2 | 10/2007 | Erickson et al. | |
| 2004/0132791 A1 | 7/2004 | Surleraux et al. | |
| 2005/0107342 A1 | 5/2005 | Erickson et al. | |
| 2005/0209301 A1 | 9/2005 | Eissenstat et al. | |
| 2005/0261364 A1 | 11/2005 | Wang et al. | |
| 2005/0267074 A1 | 12/2005 | Eissenstat et al. | |
| 2006/0258627 A1 | 11/2006 | Eissenstat et al. | |
| 2006/0293286 A1 | 12/2006 | Erickson et al. | |
| 2007/0082883 A1 | 4/2007 | Ghosh et al. | |

FOREIGN PATENT DOCUMENTS

| | | |
|---|---|---|
| WO | WO 94/04492 | 3/1994 |
| WO | WO 95/06030 | 3/1995 |
| WO | WO 96/28463 | 3/1996 |
| WO | WO 96/28418 | 9/1996 |
| WO | WO 99/67254 | 6/1999 |
| WO | WO 99/67417 | 6/1999 |
| WO | WO 99/65870 | 12/1999 |
| WO | WO 00/76961 | 12/2000 |
| WO | WO 01/25240 | 4/2001 |
| WO | WO 2004/016619 | 2/2004 |

OTHER PUBLICATIONS

Bundgaard, Drugs of the Future, 1991, 16(5), 443-458.*
Byrn et al., Pharm. Res., v. 12, n. 7, p. 945-954, 1995.*
Polymorphism in Pharmaceutical Solids, vol. 95, 1999, Taylor & Francis, Harry G. Brittain (Ed.), 427 pp. Up to p. 219 provided.*
Kubinyi (3D QSAR in Drug Design: Ligand-Protein Interactions and Molecular Similarity, vol. 2-3, Springer, 1998, 800 pages. TOC and pp. 243-244.*
Lu et al., Bioorg Med Chem Lett 13 (2003) 1821-24).*
Kirkiacharian et al., Il Farmaco 57 (2002) 703-08.*
Ghosh, A.K. Potent HIV Protease Inhibitors Incorporating High-Affinity P2-Ligands and (R)-(Hydroxyethylamino) sulfonamide Isostere. Feb. 1998, vol. 8, No. 6, pp. 687-690, especially p. 689.
Arun K. Ghosh et al., Potent HIV Protease Inhibitors Incorporating . . . , Bioorganic & Medicinal Chemistry Letters, (1998), pp. 687-690, vol. 8.
Arun K. Ghosh et al., Structure Based Design : Novel Spirocyclic . . . , Bioorganic & Medicinal Chemistry Letters, (1998), pp. 979-982, vol. 8.
Arun K. Ghosh et al., Structure-Based Design of Non-Peptide HIV Protease . . . , IL FARMACO, (2001), pp. 29-32, vol. 56(1/2).
Kazuhisa Yoshimura et al., A Potent Human Immunodeficiency Virus Type 1 . . . , Journal of Virology, (2002), pp. 1349-1358, vol. 76(3).
Final Office Action issued on Sep. 17, 2008 for U.S. Appl. No. 11/490,555.

* cited by examiner

*Primary Examiner*—Robert Havlin
(74) *Attorney, Agent, or Firm*—Perkins Coie LLP

(57) ABSTRACT

Resistance-repellent and multidrug resistant retroviral protease inhibitors are provided. Pharmaceutical composition comprising such compounds, and methods of using such compounds to treat HIV infections in mammals, are also provided.

17 Claims, No Drawings

RESISTANCE-REPELLENT RETROVIRAL PROTEASE INHIBITORS

This application claims the priority of U.S. Provisional Application No. 60/552,643, filed Mar. 11, 2004, which is incorporated into this application by reference in its entirety.

FIELD OF INVENTION

Provided herein are retroviral protease inhibitors and, more particularly, compounds, compositions and methods for inhibiting retroviral proteases. Also provided are resistance-repellent HIV protease inhibitors, compositions, and uses thereof for treating HIV infections, particularly infections caused by one or more species of drug resistant HIV strains.

BACKGROUND OF THE INVENTION

Acquired immune deficiency syndrome (AIDS) is a fatal disease, reported cases of which have increased dramatically within the past several years. Estimates of reported cases in the very near future also continue to rise dramatically. Consequently, there is a great need to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV is used hereinafter to refer to HIV viruses generically.

Specifically, HIV is known to exert a profound cytopathic effect on CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. Theoretically, there are many ways in which an agent can exhibit anti-retroviral activity. The HIV genome encodes several viral-specific enzymes, such as reverse transcriptase (RT), integrase and protease (PR); viral-specific regulatory proteins, such as tat, rev, nef and vif; and, numerous viral-specific structural proteins, and numerous viral-specific structural proteins, such as capsid, nucleocapsid, matrix, and envelope proteins. Many of these proteins are essential for viral replication. Accordingly, viral replication theoretically could be inhibited through inhibition of any one or all of the proteins involved in viral replication. In practice, however, only inhibitors of RT and PR are currently available for antiviral therapy.

Nucleoside analogues (NRTIs), such as 3'-azido-2',3'-dideoxythymidine (AZT), 2',3'-dideoxycytidine (ddC), and 2',3'-dideoxyinosine (ddI) are known to inhibit HIV RT. There also exist non-nucleoside inhibitors (NNRTIs) specific for HIV-1 RT, such as nevirapine, and efavirenz.

Retroviral PR inhibitors (PIs) have also been identified as a class of anti-retroviral agents. The retroviral PR processes polyprotein precursors into viral structural proteins and replicative enzymes. This processing is essential for the assembly and maturation of fully infectious virions. Accordingly, the design of PIs that selectively inhibit PR has been an important therapeutic goal in the treatment of HIV infections and AIDS. Strategies used in the design of HIV PIs include substrate-based, peptidomimetic, transition state-based, and structure-based drug design (Wlodawer & Erickson, *Ann. Rev. Biochem.*, 62, 543-585 (1992)).

Numerous classes of potent peptidic inhibitors of PR have been designed using the natural cleavage site of the precursor polyproteins as a starting point. These inhibitors typically are peptide substrate analogs in which the scissile P1-P1' amide bond has been replaced by a non-hydrolyzable isostere with tetrahedral geometry (Moore et al., *Perspect. Drug Dis. Design*, 1, 85 (1993); Tomaselli et al., *Int. J. Chem. Biotechnology*, 6 (1991); Huff, *J. Med. Chem.*, 34, 2305 (1991); Norbeck et al., *Ann. Reports Med. Chem.*, 26, 141 (1991); Meek, *J. Enzyme Inhibition*, 6, 65 (1992)).

The design of HIV-1 PIs based on the transition-state mimetic concept has led to the generation of a variety of peptide derivatives highly active against viral replication in vitro (Erickson et al., *Science;* 249, 527-533 (1990); Kramer et al., *Science*, 231, 1580-1584 (1986); McQuade et al., *Science*, 247, 454-456 (1990); Meek et al., *Nature (London)*, 343, 90-92 (1990); Roberts et al., *Science*, 248, 358-361 (1990)). These active agents contain a non-hydrolyzable, dipeptide isostere such as hydroxyethylene (McQuade et al., supra; Meek et al., *Nature (London)*, 343, 90-92 (1990); Vacca et al., *J. Med. Chem.*, 34, 1225-1228 (1991)) or hydroxyethylamine (Rich et al., *J. Med. Chem.*, 33, 1285-1288 (1990); Roberts et al., *Science*, 248, 358-361 (1990)) as an active moiety which mimics the putative transition state of the aspartic protease-catalyzed reaction.

Two-fold (C2) symmetric inhibitors of HIV protease represent another class of potent HIV PIs which were created by Erickson et al. on the basis of the three-dimensional symmetry of the enzyme active site (Erickson et al., supra).

Typically, the usefulness of currently available HIV PIs in the treatment of AIDS has been limited by relatively short plasma half-life, poor oral bioavailability, and the technical difficulty of scale-up synthesis (Meek et al. (1992), supra). Although these inhibitors are effective in preventing the retroviral PR from functioning, the inhibitors suffer from some distinct disadvantages. Generally, peptidomimetics make poor drugs due to their potential adverse pharmacological properties, i.e., poor oral absorption, poor stability and rapid metabolism (Plattner et al., Drug Discovery Technologies, Clark et al., eds., Ellish Horwood, Chichester, England (1990)). Furthermore, since the active site of the PR is hindered, i.e., has reduced accessibility as compared to the remainder of the PR, the ability of the inhibitors to access and bind in the active site of the PR is impaired. Those inhibitors that do bind are generally poorly water-soluble, causing distinct problems for formulation and drug delivery.

There are currently six FDA-approved PIs for clinical use—Saquinavir, Ritonavir, Indinavir, Nelfinavir, Amprenavir and Lopinavir. When used alone or in combination with RT inhibitors, PIs dramatically suppress viral replication in HIV-infected individuals. Accordingly, PIs have become "first-line" antiviral agents for the control of HIV-1 (HIV) infections and are widely used in most highly active anti-retroviral therapy (HAART) regimens (Boden & Markowitz, *Antimicrob. Agents Chemo.*, 42, 2775-2783, (1998)). Despite their success, the widespread use of PIs has led to the emergence of several thousands of genetically distinct, drug resistant HIV variants, many of which are cross-resistant to the PIs as a class (Richman, *Adv. Exp. Med. Biol.*, 392, 383-395 (1996); Boden & Markowitz (1998), supra; Shafer et al. *Ann. Intern. Med.*, 128, 906-911(1998)).

The ability of HAART to provide effective long-term anti-retroviral therapy for HIV-1 infection has become a complex issue since 40 to 50% of those who initially achieve favorable viral suppression to undetectable levels experience treatment failure (Grabar et al., *AIDS,* 14, 141-149 (1999); Wit et al., *J. Infect. Dis.*, 179, 790-798 (1999)). Moreover, 10 to 40% of antiviral therapy-naive individuals infected with HIV-1 have persistent viral replication (plasma HIV RNA>500 copies/ml) under HAART (Gulick et al., *N. Engl. J. Med.*, 337, 734-739 (1997); Staszewski et al., *N. Engl. J. Med.*, 341, 1865-1873 (1999)), possibly due to transmission of drug-resistant HIV-1 variants (Wainberg and Friedland, *JAMA*, 279, 1977-1983 (1998)). In addition, it is evident that with these anti-HIV drugs only partial immunologic reconstitution is attained in patients with advanced HIV-1 infection.

The clinical manifestations of drug resistance are viral RNA rebound and decreased CD4 cell-counts in the continued presence of drug. The majority of clinical resistance cases are due to viral adaptation through the generation and selection of mutations in the PR and RT genes. Mutant viruses can be generated through errors in reverse transcription of viral RNA, viral RNA synthesis, and recombination events (Coffin, *Retroviruses* pp.143-144, Cold Spring Harbor Laboratory Press, Plainview (1997)). Mutations within the protease gene that confer clinical drug resistance have emerged for all of the FDA-approved HIV PR inhibitors. The rapid development of drug resistance to PIs, combined with the transmissibility of drug-resistant HIV strains to newly-infected individuals, has resulted in the emergence of a new epidemic of multi-drug resistant AIDS (mdrAIDS). Multi-drug resistant AIDS is caused by a complex spectrum of genetically distinct, infectious new HIV strains that resist most or all forms of currently available treatment.

Accordingly, drug resistant HIV strains represent distinct infectious entities from a therapeutic viewpoint, and pose new challenges for drug design as well as drug treatment of existing infections. Substitutions have been documented in over 45 of the 99 amino acids of the HIV protease monomer in response to protease inhibitor treatment (Mellors, et al., *International Antiviral News*, 3, 8-13(1995); Eastman, et al., *J. Virol.*, 72, 5154-5164(1998); Kozal, et al., *Nat. Med.*, 2, 753-759(1996)). The particular sequence and pattern of mutations selected by PIs is believed to be somewhat drug-specific and often patient-specific, but high level resistance is typified by multiple mutations in the protease gene which give rise to cross-resistance to all of the PIs.

The challenge of tackling drug resistance is perhaps best illustrated by considering the dynamics of a typical HIV infection. Approximately $10^{12}$ virions are produced in an HIV infected individual every day. The mutation rate of HIV is approximately 1 per genome, which numbers $10^4$ nucleotide bases. Therefore, every nucleotide in the genome is mutated $10^8$ times per round of replication in the patient. This means that all possible single site mutations are present in at least the 0.01% level. Because of this, drugs that can be rendered ineffective with a single mutation from wild type have the shortest effective lifetime in monotherapy settings. The apparently large number of possible mutational pathways, possible mutational combinations, and the danger of generating class-specific cross resistance can make the choice of a subsequent protease inhibitor-containing combination regimen for "salvage therapy" seem very complicated and risky. Even the choice of protease inhibitor with which to initiate therapy, so-called "first-line" therapy, can be a risky enterprise that may inadvertently select for an undesired resistance pathway. Drug-naïve HIV-infected individuals pose even more of a risk for developing resistance to first-line therapies.

For the reasons outlined above, the development of new anti-HIV-1 therapeutics presents formidable challenges different from those in the design of the first line drugs, particularly in regard to consideration of selection pressure mechanisms in addition to the conventional issues of potency, pharmacology, safety, and mechanism of drug action. Indeed, HIV-1 can apparently develop resistance to any existing anti-HIV-1 therapeutic. In particular, the very features that contribute to the specificity and efficacy of RTIs and PIs provide the virus with a strategy to mount resistance (Erickson and Burt, *Annu. Rev. Pharmacol. Toxicol.*, 36, 545-571 (1996); Mitsuya and Erickson, *Textbook of AIDS Medicine*, pp.751-780, Williams and Wilkins, Baltimore (1999)), and it seems highly likely that this resistance issue will remain problematic for years to come.

Despite numerous studies of drug resistance to PIs, successful strategies to design inhibitors directly targeted against drug resistant HIV have been lacking. Instead, efforts have been directed at identifying drugs with increased potency to wild type virus, and with longer pharmacological half-lives (exemplified by Amprenavir). Another approach has been to develop PIs that are sensitive to pharmacologic "boosting" using Ritonavir, a PI that is also a potent inhibitor of the cytochrome enzymes. The latter approach, exemplified by KALETRA (a lopinavir/ritonavir combination), involves higher total drug exposures to PIs which, over time, may lead to long term, serious side effects. Several other PIs have been identified based on efforts to improve plasma half-life and bioavailability. For example, PIs incorporating the 2,5-diamino-3,4-disubstituted-1,6-diphenylhexane isostere are described in Ghosh et. al., *Bioorg. Med. Chem. Lett.*, 8, 687-690 (1998) and U.S. Pat. No. 5,728,718 (Randad et al.), both of which are incorporated herein by reference in their entirety. HIV PIs, which incorporate the hydroxyethylamine isostere, are described in U.S. Pat. No. 5,502,060 (Thompson et al.), U.S. Pat. No. 5,703,076 (Talley et al.), and U.S. Pat. No. 5,475,027 (Talley et al.).

Recent studies have revealed the structural and biochemical mechanisms by which mutations in the PR gene of HIV confer drug resistance in the presence of PIs. An important conclusion that emerges from the body of evidence on resistance to PIs is that HIV variants that exhibit cross-resistance to first-line PIs should be considered to be unique infectious agents. New therapeutic agents need to be developed to successfully treat patients infected with these viruses. New strategies for drug discovery need to be explored to develop effective protease inhibitor-based treatments for patients with multidrug resistant virus. HIV protease is one the most intensively studied molecular targets in the history of infectious disease.

More recently, new mutant strains of HIV have emerged that are resistant to multiple, structurally diverse, experimental and chemotherapeutic HIV PIs. Such mdrHIV strains are typically found in infected patients who have undergone treatment with a combination of PIs or with a series of different PIs. The number of reported cases of patients infected with mdrHIV is rising steadily. Tragically for these patients, the available options for AIDS chemotherapy and/or HIV management is severely limited or is, otherwise, completely nonexistent.

A biochemical fitness profiling strategy has recently been used to identify a novel subclass of potent PIs that have broad-based activity against mdrHIV (Gulnik et al., (1995) supra; Erickson et al., WO 99/67254; Erickson et al., WO 99/67417).

In view of the foregoing problems, there exists a need for inhibitors against drug resistant and mdrHIV strains. Further, there exists a need for inhibitors against drug resistant and multi-drug resistant HIV proteases (mdrPR). Further still, there exists a need for inhibitors of HIV that can prevent or slow the emergence of drug resistant and mdrHIV strains in infected individuals. Inhibitors with the ability to inhibit mdrHIV strains, and to slow the emergence of drug resistant strains in wild type HIV infections, are defined as "resistance-repellent" inhibitors. There also exists a need for robust methods that can be used to design "resistance-repellent" inhibitors.

SUMMARY

Provided herein are compounds that are resistance-repellent inhibitors of mdrPR, compositions containing the compounds, and methods use thereof for treating mdrHIV and wtHIV infections in salvage therapy and first-line therapy modalities.

In one embodiment, provided herein is a compound of formula I:

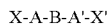    I or a pharmaceutically acceptable derivative thereof, wherein

X is a 5-7 membered non-aromatic monocyclic heterocycle, wherein said heterocycle is optionally fused or bridged with one or more 3-7 membered non-aromatic monocyclic heterocycle to form a polycyclic system, wherein any of said heterocyclic ring systems contains one or more heteroatoms selected from O, N, S, or P; wherein any nitrogen forming part of the heterocycle may optionally be substituted by R2, R3, R6, R7 or O; wherein any sulfur may be optionally be substituted by one or two oxygen atoms; wherein any P may be optionally be substituted by one or more of O, NR2, or S, and any of said ring systems optionally contains 1 to 6 substituents selected from the group consisting of R2, R3, R5, and R6;

A is ZCZNH, ZCOCONH, ZS(O)$_2$NH, ZP(O)(V)NH, CONH, COCONH, S(O)$_2$NH, P(O)(V)NH, wherein each Z is independently selected from the group consisting of NR2, O, S, or C(R2)$_2$, and V is OR2 or N(R2)$_2$;

B is

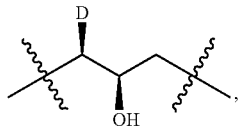

wherein D is selected from alkyl, alkenyl, alkynyl, aryl, cycloalkyl, heteroaralkyl or aralkyl, and is optionally substituted with one or more groups selected from alkyl, halo, nitro, cyano, CF$_3$, halo-C1-C6 alkyl, C3-C7 cycloalkyl, C5-C7 cycloalkenyl, R6, OR2, SR2, NHR2, OR3, SR3, NHR3, OR6, SR6, or NHR6;

A' is —N(D')-E'-, wherein D' is selected from alkyl, alkenyl, alkynyl, aryl, cycloalkyl, or aralkyl, and is optionally substituted by alkyl, halo, nitro, cyano, CF$_3$, halo-C1-C6 alkyl, O-alkyl, or S-alkyl, and E' is —CO—, —SO— or —SO$_2$—;

X' is

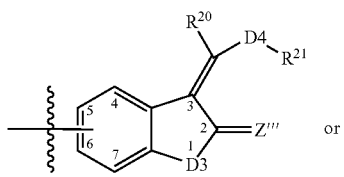 or

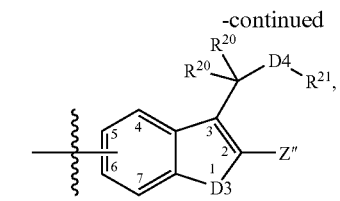

wherein each R20 is independently H, alkyl, alkenyl, alkynyl, cycloalkyl, heterocyclyl, aryl or heteroaryl, and is optionally substituted with R2, R3, R5 or R6;

Z''' is O or NR9;

Z'' is H, R, OH or NHR;

D3 is NR30, O or S;

D4 is a single bond, CR31R31, NR31, O or S;

R30 is hydrogen, OH or NHR;

R31 is hydrogen, substituted alkyl, substituted alkenyl, substituted alkynyl, substituted cycloalkyl or substituted heterocyclyl, wherein the substituents are selected from COOH, OH, NHR32 and SH where R32 is hydrogen, alkyl, alkenyl, alkynyl, cycloalkyl or heterocyclyl;

R21 is R;

or R21 and R31, together with the nitrogen atom to which they are attached, form a 3-8 membered heterocyclyl or heteroaryl ring;

or R21 and Z''', or R21 and Z'', together with the atoms to which they are attached, form a 5-8 membered cycloalkyl, aryl, heterocyclyl or heteroaryl ring;

or R31 and Z''', or R31 and Z'', together with the atoms to which they are attached, form a 6-8 membered cycloalkyl, aryl, heterocyclyl or heteroaryl ring;

or R20 and Z'', together with the atoms to which they are attached, form a 5-8 membered cycloalkyl, aryl, heterocyclyl or heteroaryl ring;

or R20, R31 or R21 forms a 5-8 membered cycloalkyl, aryl, heterocyclyl or heteroaryl ring with the C$_4$ atom or the C$_4$ substituent of the indole nucleus; or R21 is H or is selected from the group consisting of alkyl, aryl, alkenyl, alkynyl, cycloalkyl, cycloalkenyl, heterocyclyl and heteroaryl, each optionally substituted by one or more halo, haloalkyl, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl or heteroarylsulfonyl; or R21 and R31 together with the nitrogen atom to which they are attached, form a 3-8 membered unsubstituted or substituted heterocyclyl or heteroaryl ring; or R20 and R21 together form a 5-8 membered unsubstituted or substituted heterocyclyl or heteroaryl ring; and R31 is hydrogen, or is selected from the group consisting of alkyl, aryl, alkenyl, alkynyl, cycloalkyl, cycloalkenyl, heterocyclyl and heteroaryl, each optionally substituted by one or more halo, haloalkyl, hydroxy, hydroxyalkyl, R32, —COH, —COR32, —CO2H, —COOR32, —CONH2, —CONHR32, —CONR32R32, —OR32, OCOR32, —OCONHR32, OCONR32R32, cyano, nitro, amino, NHR32, NR32R32, NHCONH2, NHCONHR32, NHCONR32R32, NR32CONH2, NR32CONHR32, NR32CONR32R32, NHCOOR32, NR32COOR32, SR32, SO2NH2, SO2NHR32, SO2NR32R32, SOR32 or SO2R32;

where each R32 is independently alkyl, aryl, alkenyl, alkynyl, cycloalkyl, cycloalkenyl, heterocyclyl and heteroaryl;

wherein X' is optionally substituted with one or more substituents, each independently selected from (a)-(h) as follows:

(a) OR3, OR6, OR7, OR2;
(b) alkyl substituted by R3, R5, R6;
(c) C2-C6 alkenyl, C2-C6 alkynyl, C3-C8 cycloalkyl, C5-C8 cycloalkenyl, and heterocyclyl, which groups may be optionally substituted with one or more substituents selected from R5;
(d) aryl or heteroaryl, wherein said aryl or heteroaryl may be optionally substituted with one or more groups selected from the group consisting of aryl, heteroaryl, R2, R3, R4, and R6;
(e) C3-C7 cycloalkyl substituted by R2, R3, R5, R6;
(f) $CO_2H$ or R7;
(g) NR8R8, NR7R8, NR7R7; and
(h) $SO_nN(R8)_2$, $SO_nNR7R8$, SR8, $S(O)_nR8$; and n is 1 or 2;

R is H or alkyl, aryl, alkenyl, alkynyl, cycloalkyl, cycloalkenyl, heterocyclo, heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl;

R2 is H or C1-C6 alkyl; optionally substituted by C2-C6 alkenyl, C2-C6 alkynyl, C3-C8 cycloalkyl, C5-C8 cycloalkenyl, heterocyclo; which groups may be optionally substituted with one or more substituents selected from the group consisting of halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, =N—OR, =N—$N(R)_2$, =NR, =$NNRC(O)N(R)_2$, =$NNRCO_nR$, =$NNRS(O)_nN(R)_2$, or =$NNRS(O)_n(R)$;

or R2 is C1-C6 alkyl; substituted by aryl or heteroaryl; which groups may be optionally substituted with one or more substituents selected from the group consisting of halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$;

or R2 is C1-C6 alkyl; optionally substituted by halo, OR, ROH, R-halo, $NO_2$, CN, $CO_nR$, $CON(R)_2$, C(S)R, $C(S)N(R)_2$, $SO_nN(R)_2$, SR, $SO_nR$, $N(R)_2$, $N(R)CO_nR$, $NRS(O)_nR$, $NRC[=N(R)]N(R)_2$, $N(R)N(R)CO_nR$, $NRPO_nN(R)_2$, $NRPO_nOR$, oxo, =N—OR, =N—$N(R)_2$, =NR, =$NNRC(O)N(R)_2$, =$NNRCO_nR$, =$NNRS(O)_nN(R)_2$, or =$NNRS(O)_n(R)$;

R3 is C2-C6 alkenyl, C2-C6 alkynyl, C3-C8 cycloalkyl, C5-C8 cycloalkenyl, or heterocyclo; which groups may be optionally substituted with one or more substituents selected from the group consisting of halo, OR2, R2-OH, R2-halo, $NO_2$, CN, $CO_nR2$, $C(O)N(R2)_2$, $C(O)N(R2)N(R2)_2$, C(S)R2, $C(S)N(R2)_2$, $S(O)_nN(R2)_2$, SR2, $SO_nR2$, $N(R)_2$, $N(R2)CO_nR2$, $NR2S(O)_nR2$, $NR2C[=N(R2)]N(R2)_2$, $N(R2)N(R2)CO_nR2$, $NR2PO_nN(R2)_2$, $NR2PO_nOR2$, oxo, =N—OR2, =N—$N(R2)_2$, =NR2, =$NNRC(O)N(R2)_2$, =$NNRC(O)_nR2$, =$NNR2S(O)_nN(R2)_2$, or =$NNR2S(O)_n(R2)$;

R4 is halo, OR8, R2-OH, R3-OH, R2-halo, R3-halo, $NO_2$, CN, $CO_nR8$, $CO_nR8$, $CON(R8)_2$, $C(O)N(R8)N(R8)_2$, C(S)R8, $C(S)N(R8)_2$, $SO_nN(R8)_2$, SR8, $SO_nR8$, $N(R8)_2$, $N(R8)CO_nR8$, $NR8S(O)_nR8$, $NR8C[=N(R8)]N(R8)_2$, $N(R8)N(R8)CO_nR8$, $NR8PO_nN(R8)_2$, $NR8PO_nOR8$, OC(O)R2, OC(S)R8, $OC(O)N(R8)_2$, $OC(S)N(R8)_2$, $OPO_n(R8)_2$;

R5 is OR8, $N(R8)_2$, NHOH, N(R8)COR8, $NR8S(O)_nR8$, $NR8C[=N(R8)]N(R8)_2$, N(R8)N(R8)C(O)R8, $NR8PO_nN(R8)_2$, $NR8PO_nOR8$, R2OH, R3-OH, R2-halo, R3-halo, CN, $CO_nR8$; $CON(R8)_2$, $C(O)N(R8)N(R8)_2$, $C(S)_nR8$, $C(S)N(R8)_2$, $S(O)_nR8$, $SO_nN(R8)_2$, halo, $NO_2$, SR8, oxo, =N—OH, =N—OR8, =N—$N(R8)_2$, =NR8, =NNR8C$(O)N(R8)_2$, =$NNR8C(O_nR8$, =$NNR8S(O)_nN(R8)_2$, or =$NNR8S(O)_n(R8)$, or R3;

R6 is aryl or heteroaryl, wherein said aryl or heteroaryl may be optionally substituted with one or more groups selected from aryl, heteroaryl, R2, R3, halo, OR2, R2OH, R2-halo, $NO_2$, CN, $CO_nR2$, $C(O)N(R2)_2$, $C(O)N(R2)N(R2)_2$, $C(S)R2$, $C(S)N(R2)_2$, $S(O)_nN(R2)_2$, SR2, $SO_nR2$, $N(R)_2$, $N(R2)CO_nR2$, $NR2S(O)_nR2$, $NR2C[=N(R2)]N(R2)_2$, $N(R2)N(R2)CO_nR2$, $NR2PO_nN(R2)_2$, $NR2PO_nOR2$, OC(O)R2, OC(S)R2, $OC(O)N(R2)_2$, $OC(S)N(R2)_2$, $OPO_n(R2)_2$;

R7 is $C(O)_nR8$; C(S)R8, $C(O)N(R8)_2$, C(S)N(R8), $S(O)_nR8$, $S(O)_nN(R8)_2$;

R8 is R2, R3, or R6

R9 is alkyl optionally substituted by R3, R5, R6; C2-C6 alkenyl, C2-C6 alkynyl, C3-C8 cycloalkyl, C5-C8 cycloalkenyl, and heterocyclo, which groups may be optionally substituted with one or more substituents selected from the group consisting of —OR2, $C(O)N(R2)_2$, $S(O)_nN(2)_2$, CN, SR2, $SO_nR2$, COR2, $CO_2R2$ or $NR2C(O)R2$, R5, and R7; aryl or heteroaryl, wherein said aryl or heteroaryl may be optionally substituted with one or more groups selected from the group consisting of aryl, heteroaryl, R2, R3, R4, and R6; C3-C7 cycloalkyl optionally substituted by R2, R3, R5, R6; $CO_2H$ or R7; NR3R3, NR6R6, NR7R7, NR3R6, NR6R7, NR3R7, NR2R3, NR2R6, NR2R7, NR2R2; $SO_nN(R8)_2$, $SO_nNR7R8$, SR8, $S(O)_nR8$; and n is 1 or 2; $SO_nN(R2)_2$, $SO_nN(R3)_2$, $SO_nN(R6)_2$, $SO_nN(R7)_2$, $SO_nNR2R3$, $SO_nNR2R7$, $SO_nNR3R6$, $SO_nNR3R7$, $SO_nNR6R7$; $S(O)_mR$, $S(O)_mR3$, $S(O)_mR6$; and m is 0, 1 or 2; and each n is independently 1 or 2.

Also provided is a compound as described herein, bound in a complex with wild type or drug resistant mutant forms of HIV-1 protease. In another aspect, there is provided a method of inhibiting metabolic degradation of a retroviral protease inhibitor in a subject being treated with said inhibitor, comprising administering to the subject a degradation-inhibiting amount of a compound described herein. In another aspect of the above method, the compound is administered substantially contemporaneously with said inhibitor. In one variation of the above method, the compound is administered prior to administration of said inhibitor.

Further provided are pharmaceutical compositions, containing a compound as described herein, together with a pharmaceutically acceptable carrier, such as an additive, excipient, or diluent. The composition may further contain an additional HIV protease inhibitor and/or an HIV reverse transcriptase inhibitor.

Also provided are methods of treating a patient suffering from HIV infection by administering to the patient a compound or pharmaceutical composition as described herein.

DETAILED DESCRIPTION

A. Definitions

The invention provides 'resistance-repellent' retroviral protease inhibitors. A 'resistance-repellent' protease inhibitor ("PI") is a compound that retains inhibitory activity, or potency, over a broad spectrum of related but non-identical retroviral proteases. Examples of resistance-repellent PIs include, but are not limited to, PIs that inhibit wild type HIV-1 protease derived from any clade B virus and 1) a wild type retroviral protease from one or more different retroviruses, such as HIV-2 protease; or 2) mutant HIV-1 proteases with single active site mutations at residues 30, 82 and 84; or 3) mutant HIV-1 proteases with single active site mutations at residues 47, 48, and 50; or 4) mutant HIV-1 proteases with double active site mutations at residues 82 and 84; or 5) mutant HIV-1 proteases with double active site mutations at residues 47 and 48, 47 and 50, or 48 and 50; or 6) mutant HIV-1 proteases with double active site mutations at residues 48 and 82, 48 and 90, or 82 and 90; or 7) mutant HIV-1 proteases with three or more active site mutations in any combination at residues 32, 47, 48, 50, 82, 84 or 90.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HIV infection, in a patient. As used herein, the term "patient" refers to a mammal, including a human.

As used herein, pharmaceutically acceptable derivatives of a compound include salts, esters, enol ethers, enol esters, acetals, ketals, orthoesters, hemiacetals, hemiketals, solvates, hydrates, tautomers or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, maleates, oxalates, lactates, malates, tartrates, citrates, benzoates, salicylates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula $C=C(OR)$ where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula $C=C(OC(O)R)$ where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392). As used herein, prodrugs include phosphonates.

Also included in the present application are one or more of the various polymorphs of the compounds. A crystalline compound disclosed in the present application may have a single or may have multiple polymorphs, and these polymorphs are intended to be included as compounds of the present application. Also, where a single polymorph is noted, the polymorph may change or interconvert to one or more different polymorphs, and such polymorph or polymorph mixtures are included in the present application.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

It is also to be understood that the compounds provided herein may have tautomeric forms. All such tautomeric forms are included within the scope of the instant disclosure. For example, a 3-enamino-2-oxindole where the amino group of the enamine has a hydrogen substituent has the tautomeric form of a 3-imino-2-hydroxyindole.

The term "alkyl", alone or in combination with any other term, refers to a straight-chain or branch-chain saturated aliphatic hydrocarbon radical containing the specified number of carbon atoms, or where no number is specified, in one embodiment from 1 to about 15 (i.e. ($C_{1-15}$)alkyl), in another embodiment from 1 to about 10 carbon atoms (i.e. ($C_{1-10}$) alkyl), and in another embodiment from 1 to about 6 carbon atoms (i.e. ($C_{1-6}$)alkyl). Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, in one embodiment from 2-10 carbon atoms (i.e. ($C_{2-10}$)alkenyl) and in another embodiment, from 2-6 carbon atoms (i.e. ($C_{2-6}$)alkenyl). Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl," alone or in combination with any other term, refers to a straight-chain or branched-chain hydrocarbon radical having one or more triple bonds containing the specified number of carbon atoms, or where no number is specified, in one embodiment from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, in one embodiment from 6-15 carbon atoms (i.e. ($C_{6-15}$)aryl), and in another embodiment from 6-10 carbon atoms (i.e. ($C_{6-10}$)aryl), optionally substituted with one or more substituents selected from alkyl, alkoxy, (for example methoxy), nitro, halogen, (for example chloro), amino, carboxylate and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, means an alkyl radical as defined above in which one hydrogen atom is phenyl, benzyl, 2-phenylethyl and the like.

The term "aralkoxycarbonyl", alone or in combination, means a radical of the formula —C(O)—O-aralkyl in which the term "aralkyl" has the significance given above. An example of an aralkoxycarbonyl radical is benzyloxycarbonyl.

The term "aryloxy", alone or in combination, means a radical of the formula aryl-O— in which the term "aryl" has the significance given above.

The term "alkanoyl", alone or in combination, means an acyl radical derived from an alkanecarboxylic acid, examples of which include acetyl, propionyl, butyryl, valeryl, 4-methylvaleryl, and the like.

The term "aryloxyalkanoyl" means an acyl radical of the formula aryl-O-alkanoyl wherein aryl and alkanoyl have the significance given above.

The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-phenylbutyryl, (1-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aminocarbonyl" alone or in combination, means an amino-substituted carbonyl (carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkylalkyl radicals and the like.

The term "aminoalkanoyl" means an acyl radical derived from an amino substituted alkanecarboxylic acid wherein the amino group can be a primary, secondary or tertiary amino group containing substituents selected from the group consisting of hydrogen, cycloalkyl, cycloalkylalkyl radicals and the like, examples of which include N,N-dimethylaminoacetyl and N-benzylaminoacetyl.

The term "carbocycle" refers to a non-aromatic stable 3- to 8-membered carbon ring which may be saturated, mono-unsaturated or poly-unsaturated. The carbocycle may be attached at any endocyclic carbon atom which results in a stable structure. Carbocycles in one embodiment have 5-7 carbons.

The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like.

The term "cycloalkylalkyl" means an alkyl radical as defined above which is substituted by a cycloalkyl radical containing from about 3 to about 8, in one embodiment from about 3 to about 6, carbon atoms.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl.

The term "cycloalkylalkoxycarbonyl" means an acyl group derived from a cycloalkylalkoxycarboxylic acid of the formula cycloalkylalkyl-O—COOH wherein cycloalkylalkyl has the significance given above.

The term "heterocyclyl" or "heterocycle" refers to a stable 3-7 membered monocyclic heterocyclic ring or 8-11 membered bicyclic heterocyclic ring which is either saturated or partially unsaturated, and which may be optionally benzo-fused if monocyclic and which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e., +N—) by oxido and which is attached via a carbon atom. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Heterocycles include 5-7 membered monocyclic heterocycles and 8-10 membered bicyclic heterocycles. Examples of such groups imidazolinoyl, imidazolidinyl, indazolinolyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetrahydrofurodihydrofuranyl, tetrahydropyranodihydrofuranyl, dihydropyranyl, tetrahydrofurofuranyl and tetrahydropyranofuranyl.

The term "heteroaryl" refers to a stable 5-6 membered monocyclic or 8-11 membered bicyclic aromatic heterocycle where heterocycle is as defined above. Examples of such groups include imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxazolyl, isothiazolyl, furazanyl, thiazolyl, thiadiazolyl, oxathiolyl.

The term "heterocyclylalkanoyl" is an acyl radical derived from a heterocyclyl-substituted alkane carboxylic acid wherein heterocyclyl has the significance given above.

The term "heterocyclyloxycarbonyl" means an acyl group derived from heterocyclyl-O—COOH wherein heterocyclyl is as defined above.

The term "heterocyclylalkoxycarbonyl" means an acyl radical derived from heterocyclyl-substituted alkane-O—COOH wherein heterocyclyl has the significance given above.

The term "heteroaryloxycarbonyl" means an acyl radical derived from a carboxylic acid represented by heteroaryl-O—COOH wherein heteroaryl has the significance given above.

The term "halogen" means fluorine, chlorine, bromine or iodine.

The term "haloalkyl" means an alkyl with one or more of its hydrogens replaced by halogens. Haloalkyl also include perhaloalkyl groups or partially halogenated alkyl groups, including for example, halo-C1-C6 alkyl groups. Non-exclusive examples of haloalkyls include —CF$_3$, —CF$_2$CF$_3$, —CH$_2$CF$_3$, and the like.

The term "thioalkyl" means an alkyl radical having at least one sulfur atom, wherein alkyl has the significance given above. An example of a thioalkyl is CH$_3$SCH$_3$. The corresponding sulfoxide and sulfone of this thioalkyl are CH$_3$S(O)CH$_3$ and CH$_3$S(O)$_2$CH$_3$, respectively. Unless expressly stated to the contrary, the terms "—SO$_2$—" and "—S(O)$_2$—" as used herein refer to a sulfone or sulfone derivative (i.e., both appended groups linked to the S), and not a sulfinate ester.

The term "substituted", whether preceded by the term "optionally" or not, and substitutions contained in formulas of this invention, refer to the replacement of one or more hydrogen radicals in a given structure with the radical of a specified substituent. Examples of substituents include, but are not limited to, aldehydes, aliphatic, (C$_{1-10}$)alkyl, (C$_{1-10}$) alkylene, amino, amide, aryl, bicycloalkyl, carboxyl, carbonyl group, ester group, halo, oxo, hydroxy, nitro, and the like. Also, each of the substituents may be further substituted. When more than one position in a given structure may be substituted with more than one substituent selected from a specified group, the substituents may be either the same or different at every position (for example, the moiety —N(R2)(R2)). Typically, when a structure may be optionally substituted, 0-3 substitutions are included, and 0-1 substitutions are also included. In one embodiment, substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

Also within the scope of the instant disclosure is the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

B. Compounds

In one embodiment, there is provided a compound of formula I wherein one or more of R21, R31 and R20 is a hydrophobic group.

In another embodiment, the compounds are those wherein X is

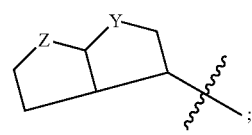

Y is O, NH, or S;
Z is O, NH, or S; and
wherein any ring carbon is optionally substituted by R2, R3, R5, or R6.

In another embodiment, the compounds are those wherein Y and Z are both O.

In another embodiment, the compounds are those wherein X is unsubstituted and has the structure:

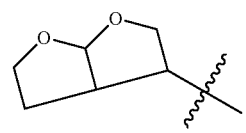

wherein any ring carbon is optionally substituted by R2, R3, R5, or R6.

In another embodiment, the compounds are those wherein X is

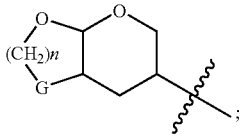

wherein
G is C, O, NR2, or S;
n is 1 or 2; and
wherein any ring carbon is optionally substituted by R2, R3, R5, or R6.

In another embodiment, the compounds are those wherein X is

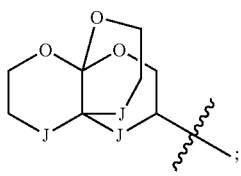

wherein
each J is independently CH$_2$, or O, and
wherein any ring carbon is optionally substituted by R2, R3, R5, or R6.

In another embodiment, the compounds are those wherein X is

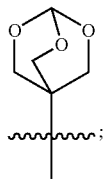

wherein any ring carbon is optionally substituted by R2, R3, R5, or R6.

In another embodiment, the compounds are those wherein X is

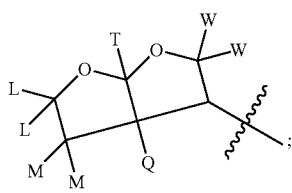

wherein
each L is independently H, lower alkyl, oxo, or L forms a carbocyclic or heterocyclic ring with M;
each M is independently H, OH, chloro, fluoro, or M forms a carbocyclic or heterocyclic ring with Q;
Q is H, OH, amino, lower alkyl, alkylamino, alkoxy, halo, or forms a 3-7-membered carbocyclic or heterocyclic ring together with T;
each W is independently H, OH, lower alkyl, halo, or spirocylopropyl; and
T is H or F, or T forms a carbocyclic or heterocyclic ring together with W.

In another embodiment, the compounds are those wherein
X is tetrahydrofurodihydrofuranyl, tetrahydrofurotetrahydrofuranyl, tetrahydropyranotetrahydrofuranyl or tetrahydropyranodihydrofuranyl.

In another embodiment, the compounds are those wherein X is

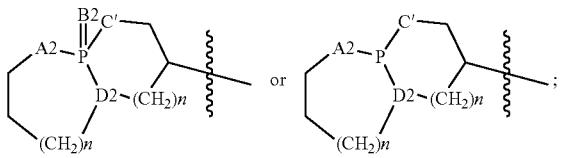

wherein A2, B2, and C' are each independently O, NR2, or S;
D2 is CH or N;
each n is independently 1 or 2; and
wherein any ring carbon is optionally substituted by R2, R3, R5, or R6.

In another embodiment, the compounds are those wherein X is

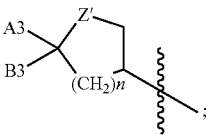

wherein
A3 is H, F or alkoxy;
B3 is F, alkoxy, lower alkyl, or A3 and B3 can form a 3-7 membered heterocyclic ring;
Z' is O, NR2, or S;
n is 1, 2 or 3; and
wherein any ring carbon is optionally substituted by R2, R3, R5, or R6.

In one variation, the compounds are those wherein A is ZCZNH. In another variation, the compounds are those wherein A is OCONH.

In one variation, the compounds are those wherein D is selected from aralkyl and heteroaralkyl, and is optionally substituted with one or more groups selected from alkyl, halo, nitro, cyano, CF$_3$, halo-C1-C6alkyl, C3-C7 cycloalkyl, C5-C7 cycloalkenyl, R6, OR2, SR2, NHR2, OR3, SR3, NHR3, OR6, SR6, or NHR6. In another variation, the compounds are those wherein D is unsubstituted aralkyl or unsubstituted heteroaralkyl. In another variation, the compounds are those wherein D is unsubstituted aralkyl. In yet another variation, the compounds are those wherein D is benzyl.

In one variation of the invention, the compounds are those wherein D' is alkyl, alkenyl, alkynyl, aryl, cycloalkyl, or aralkyl, and is optionally substituted by alkyl, halo, CF$_3$, or halo-C1-C6alkyl. In another variation, the compounds are those wherein D' is unsubstituted alkyl, cycloalkyl or aralkyl. In yet another variation, the compounds are those wherein D' is unsubstituted alkyl. In another variation, the compounds are those wherein D' is isobutyl.

In one variation, the compounds are those wherein E' is —SO—, or —SO$_2$—.

In another variation, the compounds are those wherein X' has the formula:

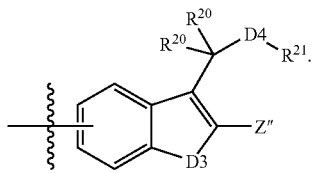

In another variation, the compounds are those wherein X' has the formula:

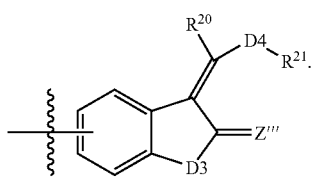

In another variation, the compounds are those wherein D3 is NR30. In yet another variation, the compounds are those wherein D3 is NH.

In another variation, the compounds are those wherein R20 is H, alkyl, alkenyl or alkynyl. In another variation, the compounds are those wherein R20 is H or alkyl. In yet another variation, the compounds are those wherein R20 is H or methyl.

In another variation, the compounds are those wherein D4 is NR31, O or S. Also, in another variation, the compounds are those wherein D4 is NR31.

In another variation, the compounds are those wherein R31 is H or alkyl. In yet another variation, the compounds are those wherein R31 is H, methyl or n-propyl.

In one variation, the compounds are those wherein R21 is hydrogen, or is selected from the group consisting of alkyl, haloalkyl, alkenyl, alkynyl, cycloalkyl, heterocyclyl, aryl, heteroaryl, or —R10-U-R31; wherein R10 is alkylene, alkenylene, alkynylene, cycloalkylene, heterocyclylene, arylene or heteroarylene;

U is NR35, O or S;

R31 is alkyl, alkenyl, alkynyl, cycloalkyl, heterocyclyl, aryl or heteroaryl; and R35 is alkyl optionally substituted by R3, R5, R6; C2-C6 alkenyl, C2-C6 alkynyl, C3-C8 cycloalkyl, C5-C8 cycloalkenyl, and heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3-C7 cycloalkyl optionally substituted by R2, R3, R5, R6; CO$_2$H or R7; NR3R3, NR6R6, NR7R7, NR3R6, NR6R7, NR3R7, NR2R3, NR2R6, NR2R7, NR2R2; SO$_n$N(R2)$_2$, SO$_n$N(R3)$_2$, SO$_n$N(R6)$_2$, SO$_n$N(R7)$_2$, SO$_n$NR2R3, SO$_n$NR2R6, SO$_n$NR2R7, SO$_n$NR3R6, SO$_n$NR3R7, SO$_n$NR6R7; S(O)$_m$R2, S(O)$_m$R3, S(O)$_m$R6, provided R2 is not H; and m is 0, 1 or 2;

wherein R21 is optionally substituted with one or more substituents each independently selected from R2, R3, R4, R5 and R6.

In one variation of the invention, the compounds are those wherein R21 is hydrogen, or is selected from the group consisting of alkyl, alkenyl, alkynyl, cycloalkyl or aryl. In another variation, the compounds are those wherein R21 is alkyl. In yet another variation, the compounds are those wherein R21 is methyl, ethyl, n-propyl, isobutyl or neopentyl.

Also provided is a compound provided herein bound in a complex with wild type or a drug resistant mutant form of HIV-1 protease.

The present invention also provides the following compounds:

{1-Benzyl-3-[(3-dimethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-dimethylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-3-({3-[(ethyl-methyl-amino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-3-({3-[1-(ethyl-methyl-amino)-ethylidene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{3-[(methyl-propyl-amino)-methylene]-2-oxo-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{3-[1-(methyl-propyl-amino)-ethylidene]-2-oxo-2,3-dihydro-1H-indole-5-sulfonyl}-amino)-propyl]-carbamic acid hexahydro-furo[2,3-b]furan-3-yl ester;

{1-Benzyl-3-[(3-diethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-diethylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

{1-Benzyl-3-[(3-dipropylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-dipropylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

{1-Benzyl-2-hydroxy-3-[isobutyl-(2-oxo-3-piperidin-1-ylmethylene-2,3-dihydro-1H-indole-5-sulfonyl)-amino]-propyl}-carbamic acid hexahydro-furo[2,3-b]furan-3-yl ester;

(1-Benzyl-2-hydroxy-3-{isobutyl-[2-oxo-3-(1-piperidin-1-yl-ethylidene)-2,3-dihydro-1H-indole-5-sulfonyl]-amino}-propyl)-carbamic acid hexahydro-furo[2,3-b]furan-3-yl ester;

{1-Benzyl-2-hydroxy-3-[isobutyl-(2-oxo-3-piperazin-1-ylmethylene-2,3-dihydro-1H-indole-5-sulfonyl)-amino]-propyl}-carbamic acid hexahydro-furo[2,3-b]furan-3-yl ester;

{1-Benzyl-2-hydroxy-3-[isobutyl-(3-morpholin-4-ylmethylene-2-oxo-2,3-dihydro-1H-indole-5-sulfonyl)-amino]-propyl}-carbamic acid hexahydro-furo[2,3-b]furan-3-yl ester;

{3-[(3-Aminomethylene-2-oxo-2,3-dihydro-1H-indole-5-sulfonyl)-isobutyl-amino]-1-benzyl-2-hydroxy-propyl}-carbamic acid hexahydro-furo[2,3-b]furan-3-yl ester;

(3-{[3-(1-Amino-ethylidene)-2-oxo-2,3-dihydro-1H-indole-5-sulfonyl]-isobutyl-amino}-1-benzyl-2-hydroxy-propyl)-carbamic acid hexahydro-furo[2,3-b]furan-3-yl ester;

{1-Benzyl-2-hydroxy-3-[isobutyl-(3-methylaminomethylene-2-oxo-2,3-dihydro-1H-indole-5-sulfonyl)-amino]-propyl}-carbamic acid hexahydro-furo[2,3-b]furan-3-yl ester;

(1-Benzyl-2-hydroxy-3-{isobutyl-[3-(1-methylamino-ethylidene)-2-oxo-2,3-dihydro-1H-indole-5-sulfonyl]-amino}-propyl)-carbamic acid hexahydro-furo[2,3-b]furan-3-yl ester;

{1-Benzyl-3-[(3-ethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-ethylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-2-hydroxy-3-(isobutyl-{2-oxo-3-[(2,2,2-trifluoro-ethylamino)-methylene]-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{2-oxo-3-[1-(2,2,2-trifluoro-ethylamino)-ethylidene]-2,3-dihydro-1H-indole-5-sulfonyl}-amino)-propyl]-carbamic acid hexahydro-furo[2,3-b]furan-3-yl ester;

[1-Benzyl-2-hydroxy-3-({3-[(2-hydroxy-ethylamino)-methylene]-2-oxo-2,3-dihydro-1H-indole-5-sulfonyl}-isobutyl-amino)-propyl]-carbamic acid hexahydro-furo[2,3-b]furan-3-yl ester;

[1-Benzyl-2-hydroxy-3-({3-[1-(2-hydroxy-ethylamino)-ethylidene]-2-oxo-2,3-dihydro-1H-indole-5-sulfonyl}-isobutyl-amino)-propyl]-carbamic acid hexahydro-furo[2,3-b]furan-3-yl ester;

[1-Benzyl-2-hydroxy-3-(isobutyl-{3-[(2-methoxy-ethylamino)-methylene]-2-oxo-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{3-[1-(2-methoxy-ethylamino)-ethylidene]-2-oxo-2,3-dihydro-1H-indole-5-sulfonyl}-amino)-propyl]-carbamic acid hexahydro-furo[2,3-b]furan-3-yl ester;

[1-Benzyl-3-({3-[(2-dimethylamino-ethylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-3-({3-[1-(2-dimethylamino-ethylamino)-ethylidene]-2-oxo-2,3-dihydro-1H-indole-5-sulfonyl}-isobutyl-amino)-2-hydroxy-propyl]-carbamic acid hexahydro-furo[2,3-b]furan-3-yl ester;

(1-Benzyl-2-hydroxy-3-{isobutyl-[3-(isopropylamino-methylene)-2-oxo-2,3-dihydro-1H-indole-5-sulfonyl]-amino}-propyl)-carbamic acid hexahydro-furo[2,3-b]furan-3-yl ester;

(1-Benzyl-2-hydroxy-3-{isobutyl-[3-(1-isopropylamino-ethylidene)-2-oxo-2,3-dihydro-1H-indole-5-sulfonyl]-amino}-propyl)-carbamic acid hexahydro-furo[2,3-b]furan-3-yl ester;

{1-Benzyl-2-hydroxy-3-[isobutyl-(2-oxo-3-propylaminomethylene-2,3-dihydro-1H-indole-5-sulfonyl)-amino]-propyl}-carbamic acid hexahydro-furo[2,3-b]furan-3-yl ester;

(1-Benzyl-2-hydroxy-3-{isobutyl-[2-oxo-3-(1-propylamino-ethylidene)-2,3-dihydro-1H-indole-5-sulfonyl]-amino}-propyl)-carbamic acid hexahydro-furo[2,3-b]furan-3-yl ester;

{1-Benzyl-2-hydroxy-3-[isobutyl-(2-oxo-3-pyrrolidin-2-ylidene-2,3-dihydro-1H-indole-5-sulfonyl)-amino]-propyl}-carbamic acid hexahydro-furo[2,3-b]furan-3-yl ester;

{1-Benzyl-3-[(3-butylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-butylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

(1-Benzyl-2-hydroxy-3-{isobutyl-[3-(isobutylamino-methylene)-2-oxo-2,3-dihydro-1H-indole-5-sulfonyl]-amino}-propyl)-carbamic acid hexahydro-furo[2,3-b]furan-3-yl ester;

(1-Benzyl-2-hydroxy-3-{isobutyl-[3-(1-isobutylamino-ethylidene)-2-oxo-2,3-dihydro-1H-indole-5-sulfonyl]-amino}-propyl)-carbamic acid hexahydro-furo[2,3-b]furan-3-yl ester;

(1-Benzyl-3-{[3-(tert-butylamino-methylene)-2-oxo-2,3-dihydro-1H-indole-5-sulfonyl]-isobutyl-amino}-2-hydroxy-propyl)-carbamic acid hexahydro-furo[2,3-b]furan-3-yl ester;

(1-Benzyl-3-{[3-(1-tert-butylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-3-({3-[(2,2-dimethyl-propylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-3-({3-[1-(2,2-dimethyl-propylamino)-ethylidene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{3-[(2-methyl-butylamino)-methylene]-2-oxo-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{3-[(3-methyl-butylamino)-methylene]-2-oxo-2,3-dihydro-1H-indole-5-sulfonyl}-amino)-propyl]-carbamic acid hexahydro-furo[2,3-b]furan-3-yl ester;

[1-Benzyl-3-({3-[(3,3-dimethyl-butylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{3-[(1-isopropyl-2-methyl-propylamino)-methylene]-2-oxo-2,3-dihydro-1H-indole-5-sulfonyl}-amino)-propyl]-carbamic acid hexahydro-furo[2,3-b]furan-3-yl ester;

{1-Benzyl-2-hydroxy-3-[isobutyl-(2-oxo-3-phenylaminomethylene-2,3-dihydro-1H-indole-5-sulfonyl)-amino]-propyl}-carbamic acid hexahydro-furo[2,3-b]furan-3-yl ester;

(1-Benzyl-3-{([3-(benzylamino-methylene)-2-oxo-2,3-dihydro-1H-indole-5-sulfonyl]-isobutyl-amino}-2-hydroxy-propyl)-carbamic acid hexahydro-furo[2,3-b]furan-3-yl ester;

(1-Benzyl-3-{[3-(1-benzylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-3-({3-[(cyclohexylmethyl-amino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

{1-Benzyl-2-hydroxy-3-[isobutyl-(2-oxo-3-{[(pyridin-4-ylmethyl)-amino]-methylene}-2,3-dihydro-1H-indole-5-sulfonyl)-amino]-propyl}-carbamic acid hexahydro-furo[2,3-b]furan-3yl ester;

(1-Benzyl-2-hydroxy-3-{isobutyl-[2-oxo-3-(phenethylamino-methylene)-2,3-dihydro-1H-indole-5-sulfonyl]-amino}-propyl)-carbamic acid hexahydro-furo[2,3-b]furan-3-yl ester;

[1-Benzyl-3-({3-[(2-cyclohex-1-enyl-ethylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{2-oxo-3-[(2-pyridin-2-yl-ethylamino)-methylene]-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{2-oxo-3-[(2-phenyl-propylamino)-methylene]-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{2-oxo-3-[(4-phenyl-butylamino)-methylene]-2,3-dihydro-1H-indole-5-sulfonyl}-amino)-propyl]-carbamic acid hexahydro-furo[2,3-b]furan-3-yl ester;

{1-Benzyl-2-hydroxy-3-[isobutyl-(3-nonylaminomethylene-2-oxo-2,3-dihydro-1H-indole-5-sulfonyl)-amino]-propyl}-carbamic acid hexahydro-furo[2,3-b]furan-3-yl ester; and (1-Benzyl-2-hydroxy-3-{[3-(1-hydroxy-ethylidene)-2-oxo-2,3-dihydro-1H-indole-5-sulfonyl]-isobutyl-amino}-propyl)-carbamic acid hexahydro-furo[2,3-b]furan-3-yl ester; and the pharmaceutically acceptable salts thereof, as single stereoisomers or mixtures of stereoisomers.

The invention also provides compounds wherein the compound is in the form of a pharmaceutically acceptable salt, biohydrolyzable ester, amide, or carbamate, solvate, hydrate or prodrug thereof. The biohydrolyzable ester may be a carboxylic ester, phosphonate ester, for example, or any ester that may be cleaved to provide the biologically active species. Also provided is the above compound that is present as a mixture of stereoisomers, or a single isomer. As noted herein, a single isomer may be a single diastereomer or a single enantiomer. Unless a particular stereochemistry is specified, recitation of a compound by its name or as represented in a drawing is intended to include all possible stereoisomers (e.g., enantiomers or diastereomers depending on the number of chiral centers in the compound), independent of whether the compound is present as an individual isomer or as a mixture of isomers. Further, unless otherwise specified, recitation of a compound by its name or represented in a drawing is intended to encompass all possible resonance forms as well as their tautomers.

The invention also provides a pharmaceutical composition comprising, as an active ingredient, any one of the above compounds. In another variation, the composition is a solid formulation adapted for oral administration. In one variation, the pharmaceutical composition is a tablet. In another variation, the composition is a liquid formulation adapted for oral administration. In yet another variation, the composition is a liquid formulation adapted for parenteral administration.

In one embodiment, the pharmaceutical composition comprising any compound of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, and intrathecally.

The invention also provides a pharmaceutical composition, containing a compound provided herein and a pharmaceutically acceptable additive, excipient, or diluent.

In one embodiment, the invention provides a pharmaceutical composition, containing a compound provided herein and another antiretroviral agent. In another embodiment, the invention provides a pharmaceutical composition, containing a compound provided herein and a second HIV inhibitor.

In another embodiment, the invention provides a pharmaceutical composition, containing a compound provided herein and an additional HIV protease inhibitor. Also provided is a pharmaceutical composition, containing a compound provided herein and an HIV reverse transcriptase inhibitor. Further, the invention also provides a method of treating a patient suffering from HIV infection, involving administering to said patient a compound provided herein.

In yet another embodiment, the invention provides a method of treating a patient suffering from HIV infection, involving administering to said patient a composition provided herein. Also provided are methods of treating a patient suffering from a multi-drug resistant HIV infection. In addition, the invention also provides a method of inhibiting an HIV protease, involving contacting the HIV protease with a compound provided herein. Also provided is a method of inhibiting an HIV protease, involving contacting the HIV protease with a composition provided herein.

In another embodiment, the invention provides methods of combination therapy involving administering a compound or composition provided herein and a cytochrome P450 inhibitor.

C. Preparation of the Compounds

The instant compounds may be easily prepared according to those synthetic methods set forth in U.S. Pat. No. 6,319,946 to Hale et al., the disclosure of which is incorporated herein by reference in its entirety. These methods will be evident to those of ordinary skill in the art.

The following scheme may be followed to synthesize the instant compounds where the X substituent can be being varied. In this scheme P is a standard amine protecting group such as Boc or Cbz. The amine is reacted with the epoxide as described previously (*J. Med. Chem.* 36, 288-291 (93)). The resulting aminoalcohol is reacted with an activated sulfonic acid derivative where X is a leaving group such as halo, an activated alcohol, or a sulfonate. The protecting group is then removed from 3 and the resulting amino alcohol 4 is reacted with an activated oxycarbonyl derivative 5 (where Y is a leaving group such as halo or an activated alcohol) to give target compound 6. Compound 5 is generated from the corresponding alcohol

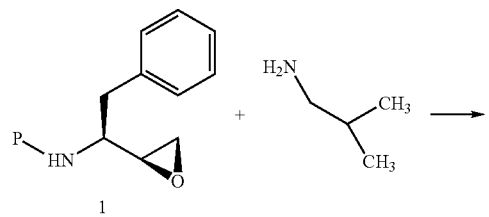
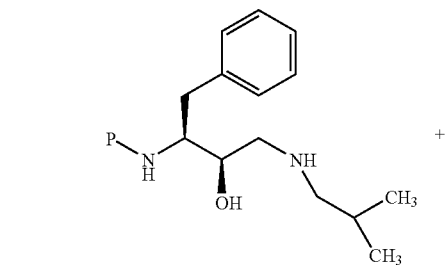
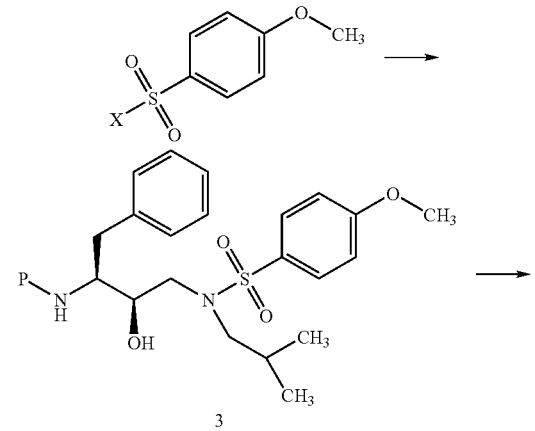
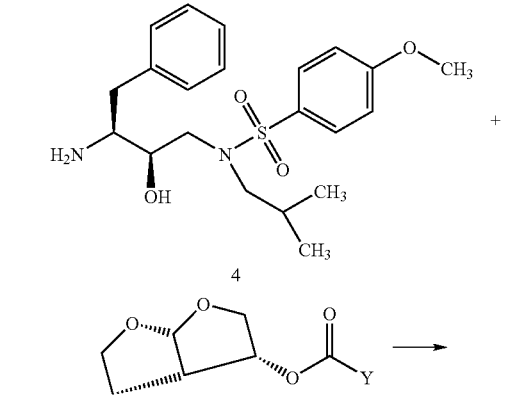
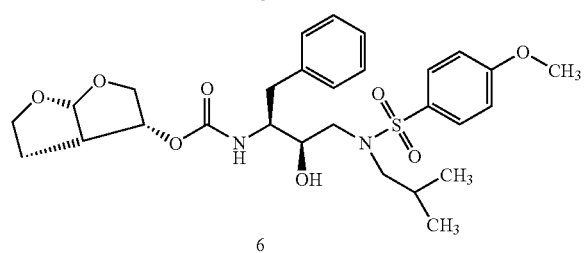

by reacting with an acid chloride or an activated ester under standard conditions and is either isolated or used in situ.

A diprotected amino epoxide such as (N,N-dibenzyl) may also be used as can an azido group that will eventually be reduced to an amine. In certain examples the activated sulfonyl derivative may be reacted with the amine and the resulting sulfonamide reacted with the epoxide under basic conditions.

A second representative synthesis can be used when exploring variations of X'. Here instead of being sulfonylated, amino alcohol 2 can be N-protected by a group that is not removed by removing P, for example P is Boc and P' is carbobenzyloxy. The di-protected 7 is then deprotected to give 8 which is reacted as above to give 9. Following deprotection of 9 various X' groups may be introduced via the activated sulfonyl derivatives in a similar fashion as described above.

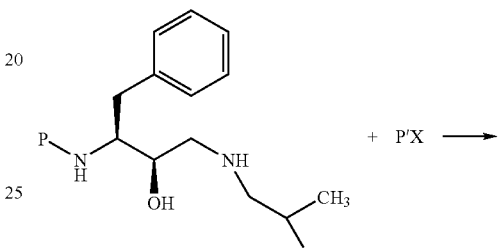
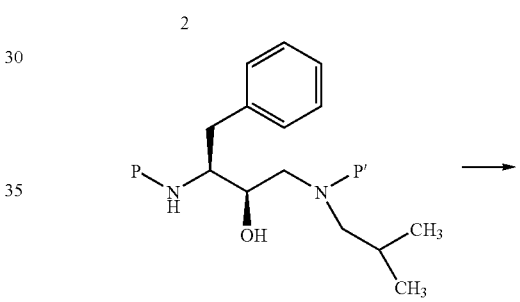
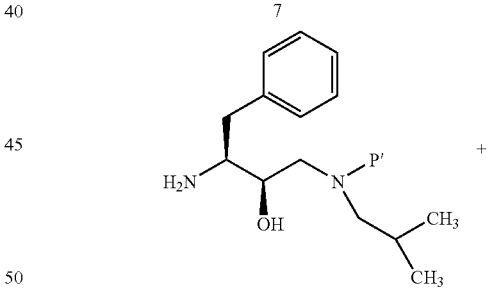
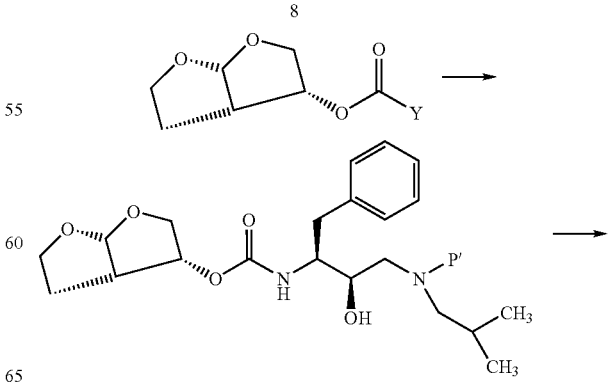

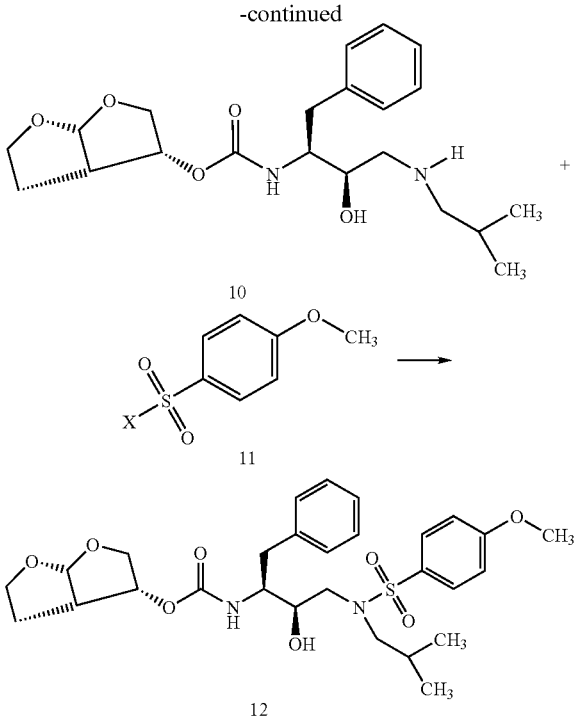

An example of a synthesis of X with a third fused ring is shown below. This olefinic tricyclic system has already been described by McElvain, et al. *JACS* 77, 5601 (1955). Anti-Markownikov addition of water across the double bond using standard conditions can provide the target alcohol. It is noteworthy that these authors showed that the unsubstituted tricyclic system had unusual acid stability, which may help prolong the activity of our target compounds.

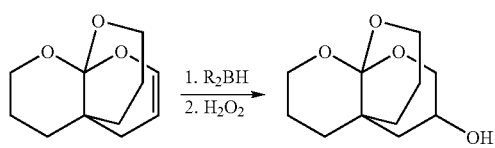

The synthesis of a bicyclo[2.2.0] system can proceed in a similar fashion as has been described Padias, et al. *J.O.C.* 52, 5305 (1987) for a homologous analog. R can either be H or a protecting group such as benzyl that can subsequently be removed under standard conditions. Protic (e.g. toluenesulfonic) or Lewis (e.g. scandium triflate) acids can be used for the condensation.

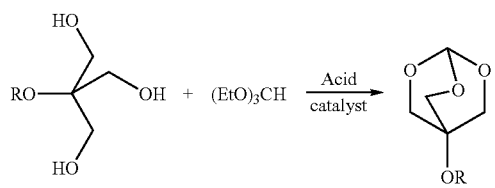

The synthesis of a representative phosphorus containing bicyclic compound is described herein. Similar chemistry has been described by Arnold, et al. in *Ang. Chem* 70, 539 (1958) and Dankiewicz, et al. in *JACS* 101, 7712 (1979). The R group in the target shown may either be H or a protecting group such as benzyl that can subsequently be removed.

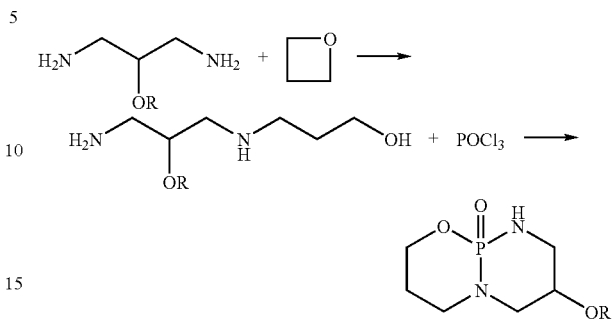

D. Pharmaceutical Compositions

The instant invention also contemplates compositions which can be administered orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like.

The compounds of the present invention-are useful in the treatment of individuals infected by HIV and for the prophylaxis of these individuals. The present invention may be useful in the treatment of mammals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (POL), as well as chronic CNS diseases caused by retroviruses, such as, for example HIV-mediated dementia and multiple sclerosis.

As a solid formulation for oral administration, the instant composition may be in the form of powders, granules, tablets, pills and capsules. In these cases, the instant compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

As used herein, "non-orally" includes subcutaneous injection, intravenous injection, intramuscular injections, intraperitoneal injection or instillation. Injectable preparations, for example, sterile injectable aqueous suspensions or oil suspensions can be prepared by known procedures in the fields concerned, using a suitable dispersant or wetting agent and suspending agent. The sterile injections may be, for example, a solution or a suspension, which is prepared with a non-toxic diluent administrable non-orally, such as an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides.

The instant pharmaceutical compositions may be formulated for nasal aerosol or inhalation and may be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug.

Examples of liquid preparations for oral administration include pharmaceutically acceptable emulsions, syrups, elixirs, suspensions and solutions, which may contain an inactive diluent, for example, water.

The pharmaceutical composition may be easily formulated for topical administration with a suitable ointment containing one or more of the instant compounds suspended or dissolved in a carrier, which include mineral oil, liquid petroleum, white petroleum, propylene glycol, polyoxyethylene polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetearyl alcohol, 2-octyldodecanol, benzyl alcohol and water.

Dosages of the instant compounds are dependent on age, body weight, general health conditions, sex, diet, dose interval, administration routes, excretion rate, combinations of drugs and conditions of the diseases treated, while taking these and other necessary factors into consideration. Generally, dosage levels of between about 10 μg per day to about 10,000 mg per day, preferably between about 10 mg per day to about 5,000 mg per day, also preferably between about 100 mg per day to about 1,000 mg per day of the compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy.

The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 0.05% to about 95% active compound (w/w). Preferably, such preparations contain from about 10% to about 80% active compound. The desired unit dose of the composition of this invention is administered once or multiple times daily.

Accordingly, a preferred embodiment the instant invention also contemplates compositions and formulations comprising one or more of the instant compounds in combination with one or more other HIV protease inhibitors, reverse transcriptase inhibitors, or non-nucleoside reverse transcriptase inhibitors.

The compounds of this invention may be administered to an uninfected or HIV-infected patient either as a single agent or in combination therapy with other anti-viral agents which interfere with the replication cycle of HIV in order to increase the therapeutic effect of these compounds. Thus, the present invention also relates to compositions comprising a compound of the present invention, and another antiretroviral compound as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, 5-helix, D-peptide ADS-Ji; co-receptor binding inhibitors, such as, for example, AMD 3100, AMD-3465, AMD7049, AMD3451 (Bicyclams), TAK 779; SHC-C (SCH351125), SHC-D, PRO-140RT inhibitors, such as, for example, foscamet and prodrugs; nucleoside RTIs, such as, for example, AZT, 3TC, DDC, DDI, D4T, Abacavir, FTC, DAPD, dOTC, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, DPC 961, DPC963, DPC082, DPCO83, calanolide A, SJ-1366, TSAO, 4"-deaminated TSAO, MV150, MV026048; RNAse H inhibitors, such as, for example, SPI093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMC114, maslinic acid, U-140690; glycosylation inhibitors, such as, for example, castanospermine, deoxynojirimycine.

The combination may in some cases provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, HE-2000 and naltrexone) with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate HIV infection and its symptoms.

Such combination therapy in different formulations, may be administered simultaneously, separately or sequentially. Alternatively, such combination may be administered as a single formulation, whereby the active ingredients are released from the formulation simultaneously or separately.

The compounds of the present invention may also be administered in combination with modulators of the metabolism following application of the drug to an individual. These modulators include compounds that interfere with the metabolism at cytochromes, such as cytochrome P450. Some modulators inhibit cytochrome P450. It is known that several isoenzymes exist of cytochrome P450, one of which is cytochrome P450 3A4. Ritonavir is an example of a modulator of metabolism via cytochrome P450. Such combination therapy in different formulations, may be administered simultaneously, separately or sequentially. Alternatively, such combination may be administered as a single formulation, whereby the active ingredients are released from the formulation simultaneously or separately. Such modulator may be administered at the same or different ratio as the compound of the present invention. Preferably, the weight ratio of such modulator vs. a compound of the present invention (modulator:compound of the present invention) is 1:1 or lower, more preferably the ratio is 1:3 or lower, suitably the ratio is 1:10 or lower, more suitably the ratio is 1:30 or lower.

In order to enhance the solubility and/or the stability of the compounds of formula I in pharmaceutical compositions, α, β, or γ-cyclodextrins or their derivatives may be employed. Also co-solvents such as alcohols may improve the solubility and/or the stability of the compounds of formula I in pharmaceutical compositions. In the preparation of aqueous compositions, addition salts of the subject compounds may be more suitable due to their increased water solubility.

Appropriate cyclodextrins are α, β, or γ-cyclodextrins (CDs) or ethers and mixed ethers thereof wherein one or more of the hydroxy groups of the anhydroglucose units of the cyclodextrin are substituted with C1-C6alkyl, such as methyl, ethyl or isopropyl, e.g. randomly methylated β-CD; hydroxy C16 alkyl, particularly hydroxyethyl, hydroxypropyl or hydroxybutyl; carboxy C1-C6alkyl, particularly carboxymethyl or carboxyethyl; C1-C6alkyl-carbonyl, particularly acetyl; C1-C6 alkyloxycarbonylC1-C6alkyl or carboxyC16alkyloxyC1-C6alkyl, particularly carboxymethoxypropyl or carboxyethoxypropyl; C1-C6alkylcarbonyloxyC1-C6alkyl, particularly 2-acetyloxypropyl. Especially noteworthy as complexants and/or solubilizers are β-CD, randomly methylated β-CD, 2,6-dimethyl-β-CD, 2.-hydroxyethyl-β-CD, 2-hydroxyethyl-γ-CD, hydroxy-propyl-γ-CD and (2-carboxymethoxy)propyl-β-CD, and in particular 2-hydroxy-propyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The present compounds may be formulated in combination with a cyclodextrin or a derivative thereof as described in EP-A-721,331. Although the formulations described therein are with antifungal active ingredients, they are equally relevant for formulating compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations may also be rendered more palatable by adding pharmaceutically acceptable sweeteners and/or favors.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising a compound of formula I, and one or more pharmaceutically acceptable water-soluble polymers.

The term "a solid dispersion" defines a system in a solid state comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogeneous throughout than solid solutions. Such dispersions are not chemically and physically uniform throughout or comprise more than one phase.

The water-soluble polymer in the particles is conveniently a polymer that has an apparent viscosity of 1 to 100 mPa.s when dissolved in a 2% aqueous solution at 20° C.

Preferred water-soluble polymers are hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The present compounds may also be incorporated in hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration may depend on the condition of the subject, co-medication and the like.

The present compounds and compositions retain inhibitory activity, or potency, over a broad spectrum of related but non-identical retroviral proteases. Accordingly, in another embodiment, there is provided methods for treating or preventing viral infections. Treating or preventing refers to alleviating or hindering symptoms or effects of a viral infection in an infected animal, such as a mammal, particularly a human. Treating includes prophylaxis as well as the treatment of viral infections or symptoms of viral infections. The instant methods comprise treating an animal with a therapeutically effective amount of a compound or composition according to the instant invention. According to another embodiment, the viral infection is an HIV infection, preferably an mdrHIV infection.

Moreover, the instant compounds and compositions are particularly effective as inhibitors against drug resistant and mdrHIV strains and multi-drug resistant HIV proteases (mdrPR). Accordingly, in another embodiment, there is provided methods for inhibiting HIV protease, particularly drug resistant and multi-drug resistant HIV proteases (mdrPR), with a therapeutically effective amount of a compound or composition according to the present application.

In relation to the above, the present compounds may be used in vaccines for protecting individuals against viral, specifically, mdrHIV infections. As such, the present compounds may be employed as protease inhibitors as conventionally used in vaccines. In this regard, one or more of the present compounds may be combined with a pharmaceutically acceptable adjuvant conventionally employed in vaccines and administered in prophylactically effective amounts to protect individuals over an extended period time against HIV infection.

Surprisingly, it has been found that certain compounds of the invention are not only potent inhibitors of HIV proteases, but also potently inhibit the cytochrome P450 isozyme (CYP3A4) that is mainly responsible for oxidative degradation of HIV protease inhibitors. In light of this activity, these compounds are degraded only slowly and have extended durations of action in vivo. Moreover, these compounds are useful for "boosting" the activities of other HIV drugs by inhibiting CYP3A4-mediated degradation of those compounds.

In this connection, the present invention provides a method of improving the pharmacokinetics of a drug (or a pharmaceutically acceptable salt thereof) which is metabolized by cytochrome P450 monooxygenase comprising coadministering a compound of the instant invention or a pharmaceutically acceptable salt thereof with a second therapeutic agent. When administered in combination, the two therapeutic agents can be formulated as separate compositions which are administered at the same time or different times, or the two therapeutic agents can be administered as a single composition.

The present invention also relates to novel compositions and methods for improving the pharmacokinetics of drugs which are metabolized by cytochrome P450 monooxygenase. In addition, the present invention relates to a novel composition and a method for inhibiting retroviral proteases and in particular for inhibiting human immunodeficiency virus (HIV) protease and a composition and a method for inhibiting a retroviral infection, in particular an HIV infection.

In this connection, the present invention provides a method of improving the pharmacokinetics of a drug (or a pharmaceutically acceptable salt thereof) which is metabolized by cytochrome P450 monooxygenase comprising coadministering a compound of the instant invention or a pharmaceutically acceptable salt thereof. When administered in combination, the two therapeutic agents can be formulated as separate compositions which are administered at the same time or different times, or the two therapeutic agents can be administered as a single composition. In one aspect, when therapeutic agents are administered in combination, the dosage used may be at the therapeutic dosage or at sub-therapeutic dosages.

Drugs which are metabolized by cytochrome P450 monooxygenase and which benefit from coadministration with a compound of the instant invention include, but are not limited to, ritonavir, the immunosuppressants cyclosporine, FK-506 and rapamycin, the chemotherapeutic agents taxol and taxotere, the antibiotic clarithromycin and the HIV protease inhibitors A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hydroxy-3-(((4-methoxyphenyl)sulphonyl)(2-methylpropyl)amino)-1-(phenylmethyl)propyl)-3-methyl-L-valinamide), KNI-272, CGP 53437, CGP 57813, tipranavir, lopinavir, atazanavir, TMC-114 and U-103017.

In another embodiment, there is disclosed a method for improving the pharmacokinetics of an HIV protease inhibitor (or a pharmaceutically acceptable salt thereof) which is metabolized by cytochrome P450 monooxygenase comprising coadministering a compound of the instant invention or a pharmaceutically acceptable salt thereof. Such a combination of a compound of the instant invention or a pharmaceutically acceptable salt thereof and an HIV protease inhibitor or a pharmaceutically acceptable salt thereof which is metabolized by cytochrome P450 monooxygenase is useful for inhibiting HIV protease in humans and is also useful for inhibition, treatment or prophylaxis of an HIV infection or AIDS (acquired immune deficiency syndrome) in humans. When administered in combination, the two therapeutic agents can be formulated as separate compositions which are administered at the same time or different times, or the two therapeutic agents can be administered as a single composition.

The following examples illustrate further the present invention but, of course, should not be construed in any way of limiting its scope.

EXAMPLES

2-Oxo-2,3-dihydro-1H-indole-5-sulfonyl chloride 14[1]

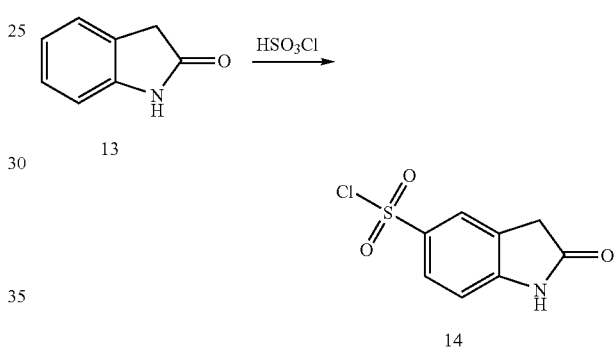

1,3-Dihydro-indol-2-one 13 (4.43 g, 33.3 mmol) was added slowly to cold chlorosulfonic acid (9 ml, 135 mmol). The reaction temperature was maintained below 30° C. during the addition. After the addition, the reaction mixture was stirred for 2 h at room temperature, then heated to 68° C. for 1 h, cooled and poured into ice water. The precipitate was washed with water and dried under vacuum to give 2-oxo-2,3-dihydro-1H-indole-5-sulfonyl chloride 14 (5.4 g, 70%). MS m/z 229 [MH]$^+$. $^1$H NMR, CD$_3$CN 8.91 (S, 1H), 7.90-7.95 (m, 2H), 7.04 (d, J=0.11, 1H), 3.57 (S,1H).

1. J. Med. Chem., 1999, vol. 42, No. 25, 5120-5130.

3-tert-Butoxycarbonylamino-2-hydroxy-4-phenyl-butyl)-isobutyl-carbamic acid benzyl ester 16

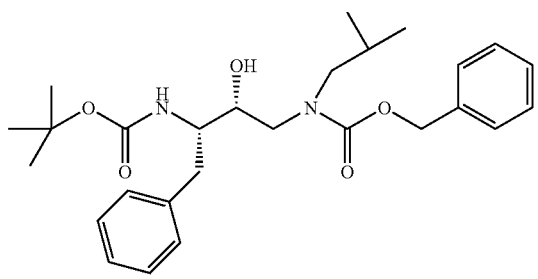

16

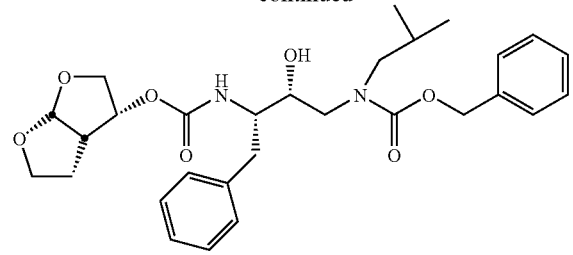

18

To (1-Benzyl-2-hydroxy-3-isobutylamino-propyl)-carbamic acid tert-butyl ester[2] 15 (94 g, 0.279 mol) in 600 ml THF was added a solution of $Na_2CO_3$ (32.5 g, 0.307 mol) in 200 ml $H_2O$. Cbz-chloride (52.4 g, 0.307 mol, 1.1 eq) dissolved in THF (100 mL) was added dropwise to the above mixture at 5-10° C. (ice bath) over the course of 1 h, after which time the mixture was stirred for additional 2 h at 10° C. Ethyl acetate (1000 ml) was then added to the reaction mixture, the organic layer was separated, washed sequentially by aqueous $NaHCO_3$, $KHSO_4$ and brine, dried over $Na_2SO_4$, filtered and concentrated in vacuo. The oily residue crystallized from EtOAc/hexane to give 3-tert-butoxycarbonylamino-2-hydroxy-4-phenyl-butyl)-isobutyl-carbamic acid benzyl ester 16 (101 g, 77%) as a white solid, m.p. 79-81° C. Elem. anal. calc: C, 68.91%, H, 8.14%, N, 5.95%; found: C, 68.91%, H, 8.27%, N, 5.85%. NMR spectrum is consistent with the structure.

2. Ghosh, et al. J.Org.Chem. 63; 18; 6146-6152 (1998).

[3-(Hexahydro-furo[2,3-b]furan-3-yloxycarbonylamino)-2-hydroxy-4-phenyl-butyl]-isobutyl-carbamic acid benzyl ester 18

(3-tert-Butoxycarbonylamino-2-hydroxy-4-phenyl-butyl)-isobutyl-carbamic acid benzyl ester 16 (7.54 g, 15 mmol) and 35 ml of 4M HCl in dioxane were stirred 30 min under an argon atmosphere. The mixture was concentrated in vacuo, and co-evaporated twice with dichloromethane. The residue was dissolved in dichloromethane (50ml) and N,N-diisopropylethylamine (6.1 ml, 35 mmol), and carbonic acid 2,5-dioxo-pyrrolidin-1-yl ester hexahydro-furo[2,3-b]furan-3-yl ester 17 (4.88g, 18 mmol) was added. The reaction mixture was stirred overnight, and then concentrated in vacuo. The residue was diluted with dichloromethane, and sequentially washed with brine, 10% $KHSO_4$, brine, saturated $NaHCO_3$, and brine, then dried over $MgSO_4$, and concentrated in vacuo. The oily residue was purified by flash chromatography using 70:30 ethyl acetate hexane as eluant, to give [3-(Hexahydro-furo[2,3-b]furan-3-yloxycarbonylamino)-2-hydroxy-4-phenyl-butyl]-isobutyl-carbamic acid benzyl ester 18 (5.8 g, 73%) as a white solid. TLC: $R_f$ 0.56 (7:3 ethyl acetate: hexane). MS m/z 527 (MH)$^+$.

Related procedure: Ghosh, et al. BMCL 687 (1998).

(1-Benzyl-2-hydroxy-3-isobutylamino-propyl)-carbamic acid hexahydro-furo[2,3-b]furan-3-yl ester 19

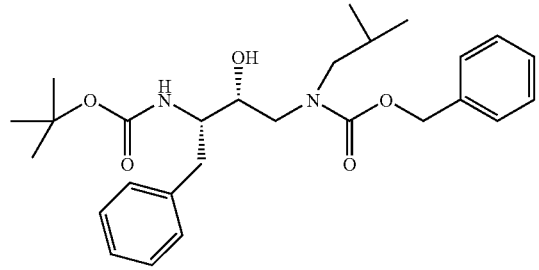

16

+

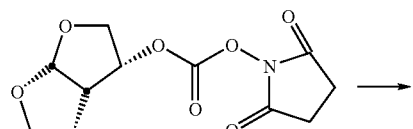

17

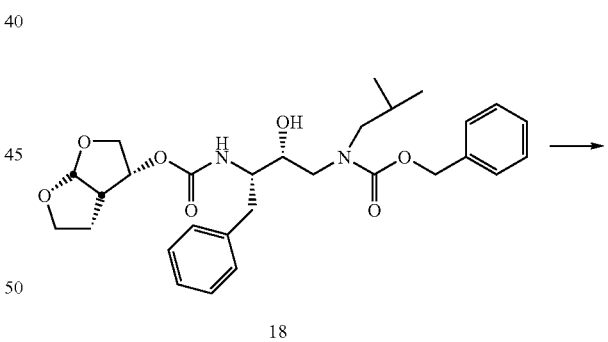

18

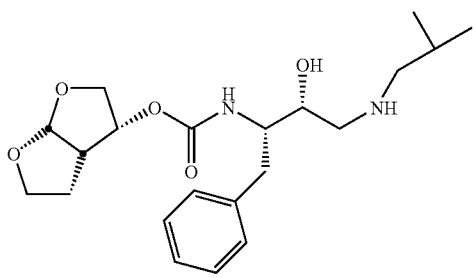

19

A mixture of [3-(hexahydro-furo[2,3-b]furan-3-yloxycarbonylamino)-2-hydroxy-4-phenyl-butyl]-isobutyl-carbamic acid benzyl ester 18 (5.5 g, 10.4 mmol) and 550 mg of 10% Pd/C in 130 ml of ethanol was stirred under a hydrogen atmosphere overnight. The catalyst was removed by filtration through Celite®, and the solution was evaporated to dryness to yield (1-benzyl-2-hydroxy-3-isobutylamino-propyl)-carbamic acid hexahydro-furo[2,3-b]furan-3-yl ester 19 (4.0 g, 97%) as a white solid. TLC: $R_f$ 0.36 (5:15:85 triethylamine:methanol:ethyl acetate). MS m/z 393 (MH)$^+$.

{1-Benzyl-2-hydroxy-3-[isobutyl-(2-oxo-2,3-dihydro-1H-indole-5-sulfonyl)-amino]-propyl}-carbamic acid hexahydro-furo[2,3-b]furan-3-yl ester 20

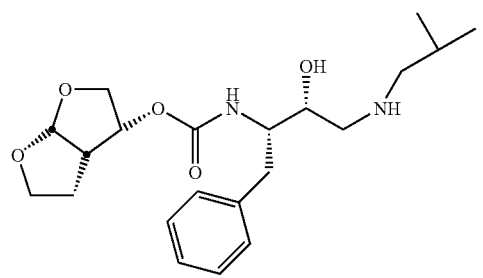

19

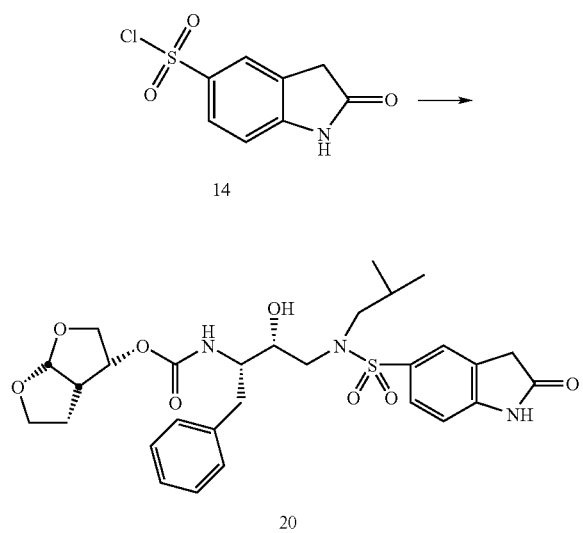

20

To a solution of (1-benzyl-2-hydroxy-3-isobutylamino-propyl)-carbamic acid hexahydro-furo[2,3-b]furan-3-yl ester 19 (59 mg, 0.15 mmol) in CH$_2$Cl$_2$ (1.6 ml) was added saturated aqueous sodium bicarbonate (0.4 ml), solid sodium bicarbonate (16 mg, 0.19 mmol), and then 2-oxo-2,3-dihydro-1H-indole-5-sulfonyl chloride 14 (42 mg, 0.18 mmol). The mixture was stirred overnight, diluted with ethyl acetate, washed with saturated brine, dried over magnesium sulfate, filtered, and concentrated in vacuo to provide the title product as a white solid, (79 mg, 90%). TLC: $R_f$ 0.33 (Ethyl acetate). MS m/z 588 (MH)$^+$. $^1$H NMR (CDCl$_3$) is consistent with the structure.

Method A

{1-Benzyl-3-[(3-dimethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester 21

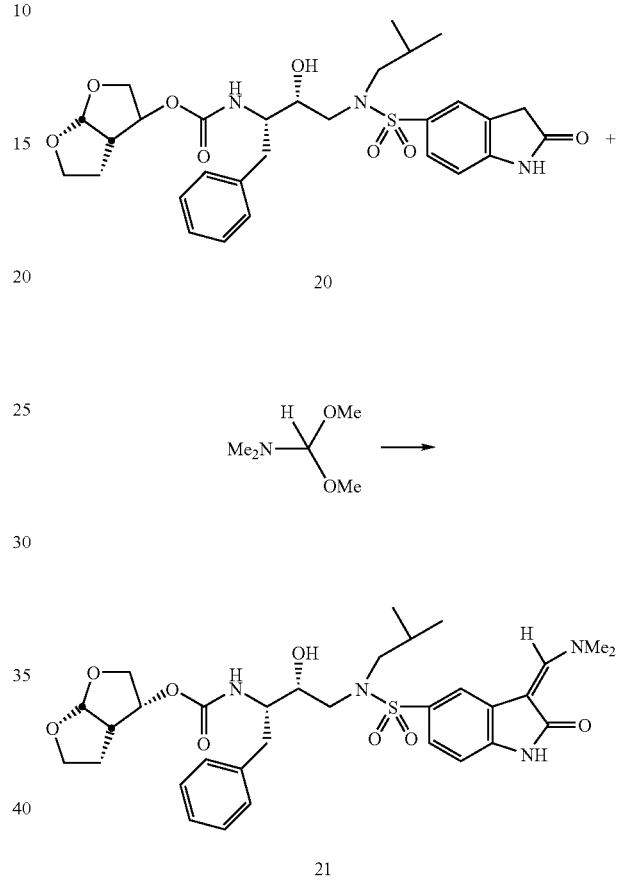

A solution of {1-benzyl-2-hydroxy-3-[isobutyl-(2-oxo-2,3-dihydro-1H-indole-5-sulfonyl)-amino]-propyl}-carbamic acid hexahydro-furo[2,3-b]furan-3-yl ester 20 (59 mg, 0.1 mmol) and N,N-dimethylformamide dimethylacetal (27 ul, 0.2 mmol) in 1 ml of chloroform was refluxed for 1 h, cooled, and concentrated in vacuo. The residue was chromatographed on silica gel, (methanol:ethyl acetate 3:97) to obtain {1-benzyl-3-[(3-dimethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester 21 (48 mg, 75%). TLC: $R_f$ 0.09 (ethyl acetate). MS m/z 643 (MH)$^+$. $^1$H NMR (CDCl$_3$) consistent with structure.

Method B

[1-Benzyl-3-({3-[(2,2-dimethyl-propylamino)-methylene]-2-oxo-2,3-dihydro-1H-indole-5-sulfonyl}-isobutyl-amino)-2-hydroxy-propyl]-carbamic acid hexahydro-furo[2,3b]furan-3-yl ester 22

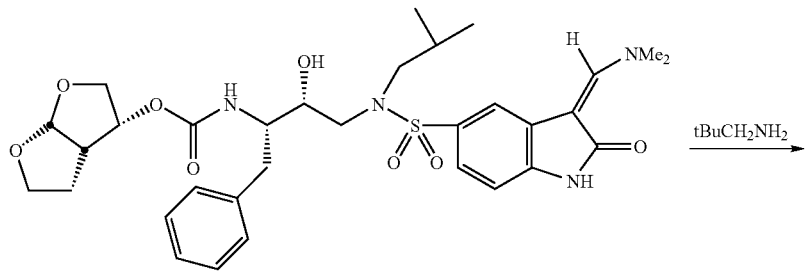

21

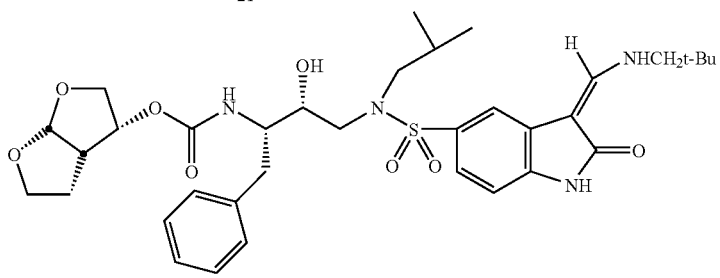

22

To a solution of {1-benzyl-3-[(3-dimethylaminomethylene-2-oxo-2,3-dihydro-1H-indole-5-sulfonyl)-isobutylamino]-2-hydroxy-propyl}-carbamic acid hexahydro-furo[2,3-b]furan-3-yl ester 21 (32mg, 0.05 mmol) in absolute ethanol (1 ml) was added neopentylamine (29 μl, 0.25 mmol). The resulting solution was stirred 22 h and then concentrated in vacuo. The residue was purified on a preparative TLC plate (20×20 cm, 500 μm) using 8:2 ethyl acetate:hexane as eluant to provide [1-benzyl-3-({3-[(2,2-dimethyl-propylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester 22 (24 mg, 70%). TLC: $R_f$ 0.63 (ethyl acetate:hexanes). MS m/z 685 (MH)$^+$. $^1$H NMR (CDCl$_3$) is consistent with structure.

Related reference J. Med. Chem., 1989, Vol.32, No.2, 437-444.

Other compounds provided herein are shown below. All compounds exhibited satisfactory mass spectra.

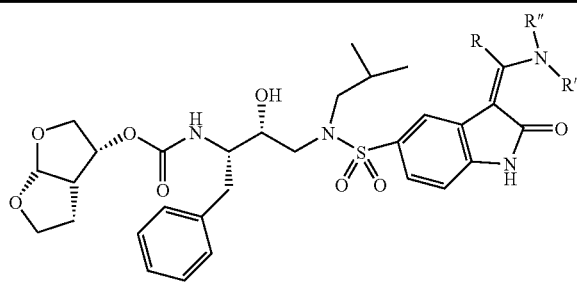

| Compound | R | R' | R'' | Reaction Type | Temperature ° C. | Time (h) | % Yield[a] |
|---|---|---|---|---|---|---|---|
| 21 | H | Me | Me | A | 61 | 1 | 75 |
| 25 | Me | Me | Me | A | 61 | 1 | 70 |
| 26 | H | Me | Et | B | 50 | 70 | 30 |
| 27 | Me | Me | Et | B | 50 | 76 | 24 |
| 28 | H | Me | Pr | B | 80 | 25 | 31 |
| 29 | Me | Me | Pr | B | 80 | 28 | 29 |
| 30 | H | Et | Et | B | 80 | 29 | 45 |
| 31 | Me | Et | Et | B | 83 | 24 | 40 |
| 32 | H | Pr | Pr | B | 83 | 24 | 28 |
| 33 | Me | Pr | Pr | B | 83 | 22 | 26 |
| 34 | H | CH2CH2CH2CH2CH2 | | B | 89 | 22 | 35 |
| 35 | Me | CH2CH2CH2CH2CH2 | | B | 89 | 22 | 25 |
| 36 | H | CH2CH2NHCH2CH2 | | B | 80 | 22 | 29 |
| 37 | H | CH2CH2OCH2CH2 | | B | 80 | 22 | 44 |
| 38 | H | H | H | B | RT | 2.5 | 83 |
| 39 | Me | H | H | B | RT | 3 | 60 |

-continued

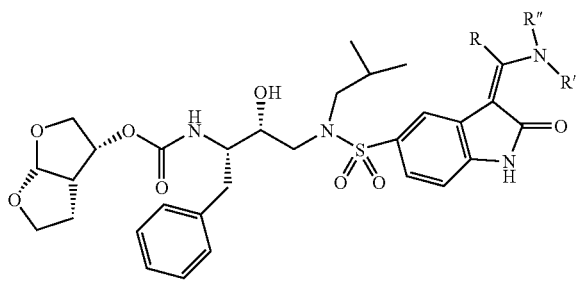

| Compound | R | R' | R" | Reaction Type | Temperature °C. | Time (h) | % Yield[a] |
|---|---|---|---|---|---|---|---|
| 40 | H | H | Me | B | RT | 2.5 | 80 |
| 41 | Me | H | Me | B | RT | 2 | 51 |
| 42 | H | H | Et | B | RT | 3 | 54 |
| 43 | Me | H | Et | B | RT | 22 | 56 |
| 44 | H | H | $CH_2CF_3$ | B | RT | 100 | 55 |
| 45 | Me | H | $CH_2CF_3$ | B | 50 | 23 | 54 |
| 46 | H | H | $CH_2CH_2OH$ | B | RT | 24 | 29 |
| 47 | Me | H | $CH_2CH_2OH$ | B | RT | 25 | 30 |
| 48 | H | H | $CH_2CH_2OMe$ | B | RT | 20 | 44 |
| 49 | Me | H | $CH_2CH_2OMe$ | B | RT | 20 | 45 |
| 50 | H | H | $CH_2CH_2NMe_2$ | B | RT | 3 | 27 |
| 51 | Me | H | $CH_2CH_2NMe_2$ | B | RT | 5 | 29 |
| 52 | H | H | iPr | B | RT | 23 | 43 |
| 53 | Me | H | iPr | B | 50 | 20 | 62 |
| 54 | H | H | Pr | B | RT | 5 | 30 |
| 55 | Me | H | Pr | B | RT | 22 | 52 |
| 56 | —$CH_2$ linked to —$CH_2CH_2$— | H | R | A | 70 | 100 | 53 |
| 57 | H | H | Bu | B | RT | 4 | 51 |
| 59 | Me | H | Bu | B | RT | 23 | 65 |
| 60 | H | H | iBu | B | RT | 2 | 42 |
| 61 | Me | H | iBu | B | RT | 53 | 48 |
| 62 | H | H | tBu | B | RT | 120 | 44 |
| 63 | Me | H | tBu | B | 55 | 120 | 39 |
| 22 | H | H | $CH_2$tBu | B | RT | 22 | 70 |
| 64 | Me | H | $CH_2$tBu | B | RT | 72 | 54 |
| 65 | H | H | 2-Me-Bu | B | RT | 17 | 43 |
| 66 | H | H | $CH_2CH_2$i-Pr | B | RT | 22 | 54 |
| 67 | H | H | $CH_2CH_2$tBu | B | RT | 5 | 46 |
| 68 | H | H | $CH(iPr)_2$ | B | 80 | 7 | 47 |
| 69 | H | H | Ph | B | 83 | 22 | 27 |
| 70 | H | H | $CH_2$Ph | B | RT | 5 | 47 |
| 71 | Me | H | $CH_2$Ph | B | RT | 23 | 67 |
| 72 | H | H | $CH_2C_6H_{11}$ | B | RT | 22 | 47 |
| 73 | H | H | $CH_2$-4-Pyr | B | RT | 23 | 55 |
| 74 | H | H | $(CH_2)_2$Ph | B | RT | 24 | 50 |
| 75 | H | H | $CH_2CH_2C_6H_{10}$ | B | RT | 24 | 42 |
| 76 | H | H | $(CH_2)_2$-2-Pyr | B | RT | 27 | 55 |
| 77 | H | H | $CH_2CH(Me)Ph$ | B | RT | 23 | 52 |
| 78 | H | H | $(CH_2)_4$Ph | B | RT | 22 | 55 |
| 79 | H | H | $(CH_2)_8CH_3$ | B | RT | 23 | 41 |
| 80 | | | | | | | Obtained by acid hydrolysis of 21 |

Additional compounds made using procedure B include:

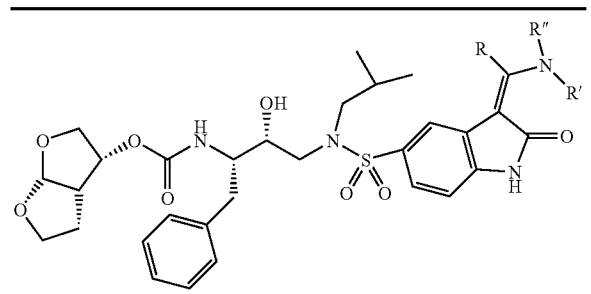

| Compound | R | R' | R" | Reaction Type |
|---|---|---|---|---|
| 81 | H | H | (CH2)2OPh | B |
| 82 | H | H | 2-CH2CH2NMe-pyrollidine | B |
| 83 | Me | H | (CH2)2-2-Pyridyl | B |
| 84 | H | Et | CH2-4-Pyridyl | B |
| 85 | H | CH2-2-Pyridyl | CH2-2-Pyridyl | B |
| 86 | H | Et | CH2-2-Pyridyl | B |
| 87 | H | H | (CH2)2-3-Pyridyl | B |
| 88 | | H | (CH2)5 linked to R | B |
| 89 | H | H | (CH2)3OEt | B |
| 90 | H | H | (CH2)2-4-Pyridyl | B |
| 91 | H | Me | (CH2)2-2-Pyridyl | B |
| 92 | H | H | (CH2)6OH | B |
| 93 | H | C6H11 | CH2-2-Pyridyl | B |
| 94 | H | H | (CH2)2SEt | B |
| 95 | | H | (CH2)4 linked to R | B |
| 96 | H | H | CH2CH2-4-morpholinyl | B |
| 97 | H | H | s-Bu | B |
| 98 | H | H | CH(Me)iPr | B |
| 99 | H | CH2CH2CH2 | CH(CO2Et)CH2 linked to R' | B |
| 100 | H | H | CH(Et)2 | B |
| 101 | H | H | CH2cyclopropyl | B |
| 102 | H | Me | cyclohexyl | B |
| 103 | H | H | CH2CH(Et)2 | B |
| 104 | H | H | CH(Me)CH2iPr | B |
| 105 | H | H | CH(Me)(CH2)2iPr | B |
| 106 | H | Et | Pr | B |
| 107 | H | H | cyclohexyl | B |
| 108 | H | H | 1-Me-Bu | B |
| 109 | H | Me | Bu | B |
| 110 | H | H | cyclopentyl | B |
| 111 | H | Me | iBu | B |
| 112 | H | H | 6-Et-2-Pyridyl | B |
| 113 | H | iBu | iBu | B |
| 114 | H | H | cyclobutyl | B |
| 115 | H | Et | iPr | B |
| 116 | H | allyl | cyclopentyl | B |
| 117 | H | H | CH2CH2NHCO2tBu | B |
| 118 | H | Et | Bu | B |
| 119 | H | H | CH2CF2CF3 | B |
| 120 | H | Et | isobutenyl | B |
| 121 | H | H | CH2CH2NHPh | B |
| 122 | H | Pr | 2-Bu | B |
| 123 | H | H | CH2-2-benzimidazolyl | B |
| 124 | H | H | CH2-2-(5-Me-Pyrazinyl) | B |
| 125 | H | H | CH2CF2CF2CF3 | B |
| 126 | H | H | (CH2)2-4-NH2Ph | B |
| 127 | H | H | (CH2)2-4-OHPh | B |
| 128 | H | H | CH2-3,5-(OMe)-4Me-2-Pyridyl | B |
| 129 | H | H | CH2-(2-Me-4-thiazolyl) | B |
| 130 | H | H | CH2-2-quinolinyl | B |
| 131 | Me | H | CH2cyclohexyl | B |
| 132 | H | H | CH2CO2tBu | B |
| 133 | H | H | CH(iPr)CO2Et | B |
| 134 | H | H | CH(CH2Ph)CO2Me | B |
| 135 | H | H | CH(CH2-4-ClPh)CO2Et | B |
| 136 | H | H | CH2CO2CH2Ph | B |
| 137 | H | H | (CH2)2CO2CH2Ph | B |
| 138 | H | CH2Ph | CH2CO2Et | B |

-continued

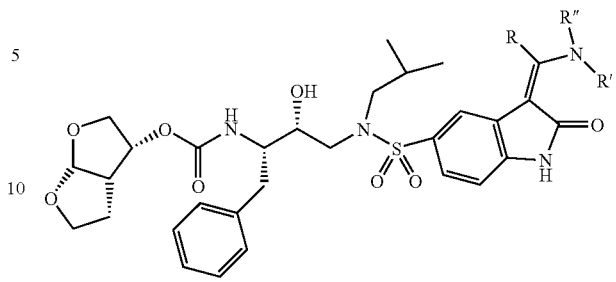

| Compound | R | R' | R" | Reaction Type |
|---|---|---|---|---|
| 139 | H | | CH2CH(CO2Me)CH2 linked to R' | B |
| 143 | H | H | Cyclopropyl | B |
| 144 | H | H | CH2-5-benzofuranyl | B |

Method C

Reaction of products prepared by the methods outlined above with acylating agents such as acetic anhydride or ethyl chloroformate provided the products below:

| | | | | |
|---|---|---|---|---|
| 140 | H | H | CO2Et (NCO2Et) | C |
| 141 | H | H | CO2Et | C |
| 142 | H | H | Ac | C |

HIV PR Inhibition Assays:

Expression and purification of WT and mutant HIV PR. Recombinant wild type and mutant HIV PRs were expressed using pET21 vector (Novagen) in E. coli cells, and purified and refolded as described previously (Gulnik et al, 1995). The cells were resuspended in 50 mM tris-HCl buffer, pH 8.0, 25 mM NaCl, 0.2% β-mercaptoethanol (buffer A), sonicated and centrifuged. Inclusion bodies were washed first with buffer A, then with buffer A containing respectively 0.1% Triton X-100, 1 M NaCl, 1 M urea, and finally with buffer A alone. Purified inclusion bodies were solubilized by addition of buffer A containing 8 M urea at room temperature. The solution was clarified by centrifugation and loaded onto 2.6×9.5 cm Q-Sepharose column. Flow-through fractions were collected and dialyzed against 3 changes of refolding buffer, which consists of 25 mM Na-phosphate, pH 7.0, 25 mM NaCl, 0.2% β-mercaptoethanol and 10% glycerol, aliquoted and stored at −80° C.

Inhibition constants were determined using the fluorogenic substrate ArgGlu(EDANS)SerGlnAsnTyr-ProIleValGlnLys(DABCYL)Arg (Amichem, USA). HIV Protease was preincubated for 0.5-1 min at ambient temperature on a 96 well plate with different concentrations of inhibitor in 0.05 M sodium phosphate buffer, pH 6.5, containing 20 mM NaCl, 2 mM DTT and 0.01% Tween-20. The reaction was initiated by the addition of substrate. Final enzyme concentration was 2-5 nM for WT and 2-30 nM for mutants. Substrate concentration was 20 uM and DMSO concentration 2%. The increase in fluorescence intensity at the emission maximum of 520 nm (excitation wavelength 340 nm, cut-off filter 495 nm) was monitored as a function of time using a Spectramax Gemini fluorescence plate reader (Molecular Devices, CA USA). The initial rate of hydrolysis was calculated by first-degree polynomial fit using SoftMAX operating software. Data were fitted to the Michaelis-Menten equation for competitive inhibitors. For tight-binding inhibitors the data were fitted by nonlinear regression analysis to the equation $$V = V_0/2E_t(\{[K_i(1+S/K_m)+I_t-E_t]^2 + 4K_i(1+S/K_m)E_t\}^{1/2} - [K_i(1+S/K_m)+I_t-E_t])$$  (Williams and Morrison, 1979)

with the program GraFit, version 5 (Erithacus Software Limited, UK), where V and $V_0$ are initial velocities with and without inhibitor, $K_m$ is the Michaelis-Menten constant and S, $E_t$ and $I_t$ are the concentrations of substrate, active enzyme and inhibitor respectively.

Antiviral Assays:

MT-4 cells were obtained from the AIDS Research and Reference Reagent Program (ARRRP, Division of AIDS, NIAID, NIH: MT-4 from Dr. D. Richman). Cells were propagated in RPMI 1640 supplemented with 10% fetal bovine serum, 50U of penicillin and 50 µg of streptomycin per ml (Invitrogen, Carlsbad Calif.). The following HIV viruses were used for testing of antiviral potency of compounds: WT=$HIV_{HXB2}$; recombinant $HIV_{HXB2}$ virus from drug resistant patient isolates; $HIV_{mutant10}$ (16 mutations); $HIV_{mutant8}$ (14 mutations); $HIV_{mutant9}$ (10 mutations).

The potency of test compound was determined as previously described (ref 1-3) with minor modifications. MT-4 cells ($1.5 \times 10^4$/ml) were exposed to 200 50 % tissue culture infective doses (TCID50) of viruses in the presence of various concentrations of test compound in 96 well microtiter plates and incubated at 37° C. for 5 days. 3-(4,5-dimethylthiazol-2-yl)-2,5-diphenytetrazolium bromide (MTT) solution was added to a final concentration of 0.75 mg/ml, and plates were incubated 1 hour. After incubation cells were dissolved in isopropanol/Triton-X 100/HCl (1000:50:25) solution. Absorbance was monitored in a microplate reader (Spectramax, Molecular Devices) at 540 nm and 690 nm. Cytotoxicity of compounds was tested in a similar assay in the absence of virus.

TABLE 1

Ki Data
Biological Data

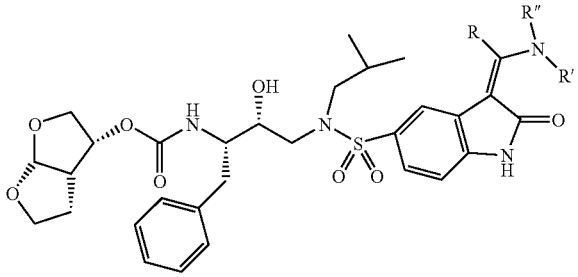

| Compd No. | R | R' | R'' | Ki WT | Ki Mutant 8 | Ki Mutant 9 | Ki Mutant 10 |
|---|---|---|---|---|---|---|---|
| 21 | H | Me | Me | <0.10 | <0.30 | <0.10 | <1.0 |
| 41 | Me | H | Me | <0.10 | <0.30 | <0.10 | <1.0 |
| 32 | H | Pr | Pr | <0.10 | <0.30 | <0.10 | <1.0 |
| 43 | Me | H | Et | <0.10 | <0.30 | <0.10 | <1.0 |
| 60 | H | H | iBu | <0.10 | <0.30 | 0.15 | <1.0 |
| 22 | H | H | $CH_2tBu$ | <0.10 | <0.30 | 0.15 | <1.0 |
| 45 | Me | H | $CH_2CF_3$ | <0.10 | <0.30 | <0.10 | 3.1 |
| 57 | H | H | Bu | <0.10 | <0.30 | 0.19 | <1.0 |
| 78 | H | H | $(CH_2)_4Ph$ | <0.10 | <0.30 | <0.10 | <1.0 |
| 66 | H | H | $CH_2CH_2iPr$ | <0.10 | <0.30 | <0.10 | <1.0 |
| 72 | H | H | $CH_2$cyclohexyl | <0.10 | <0.30 | <0.10 | <1.0 |
| 76 | H | Et | $CH_2CH_2$-2-Pyr | <0.10 | <0.30 | <0.10 | <1.0 |
| 101 | H | H | $CH_2$cyclopropyl | 0.11 | <0.30 | 0.19 | <1.0 |
| 104 | H | H | $CH(Me)CH_2iPr$ | 0.17 | <0.30 | 0.25 | 1.3 |
| 106 | H | Et | Pr | <0.10 | <0.30 | <0.10 | <1.0 |
| 107 | H | H | cyclohexyl | <0.10 | <0.30 | 0.21 | 1.2 |
| 108 | H | H | 1-Me-Bu | <0.10 | <0.30 | <0.10 | <1.0 |
| 112 | H | H | 6-Et-2-Pyr | <0.10 | <0.30 | 0.17 | 6.4 |
| 113 | H | iBu | iBu | <0.10 | <0.30 | 0.21 | 2.9 |
| 114 | H | H | cyclobutyl | <0.10 | <0.30 | 0.15 | 1.2 |
| 116 | H | allyl | cyclopentyl | <0.10 | <0.30 | <0.10 | <1.0 |
| 118 | H | Et | Bu | <0.10 | <0.30 | <0.10 | 1.9 |
| 120 | H | Et | isobutenyl | <0.10 | <0.30 | <0.10 | 1.5 |
| 125 | H | H | $CH_2CF_2CF_2CF_3$ | <0.10 | <0.30 | 0.17 | 1.2 |
| 128 | H | H | $CH_2$-3,5-(OMe)-4-Me-2-Pyridyl | <0.10 | <0.30 | <0.10 | <1.0 |
| 130 | H | H | $CH_2$-2-quinolinyl | 0.10 | <0.30 | <0.10 | <1.0 |
| 133 | H | H | $CH(iPr)CO_2Et$ | 0.14 | <0.30 | 0.40 | 3.1 |
| 138 | H | $CH_2Ph$ | $CH_2CO_2Et$ | <0.10 | <0.30 | 0.11 | 1.9 |

All values are in nM.

TABLE 2

IC$_{50}$ Data

| Compd No. | R | R' | R" | IC$_{50}$ WT | IC$_{50}$ Mutant 8 | IC$_{50}$ Mutant 9 | IC$_{50}$ Mutant 10 |
|---|---|---|---|---|---|---|---|
| 21 | H | Me | Me | 93 | 90 | 65 | 70 |
| 41 | Me | H | Me | 10 | 29 | 17 | 56 |
| 32 | H | Pr | Pr | 10 | 24 | 12 | 58 |
| 43 | Me | H | Et | 7.0 | 23 | 9.0 | 65 |
| 60 | H | H | iBu | 7.5 | 16 | 9.5 | 33 |
| 22 | H | H | CH$_2$tBu | 4.5 | 13 | 9.5 | 27 |
| 45 | Me | H | CH$_2$CF$_3$ | 13 | 26 | 13 | 52 |
| 57 | H | H | Bu | 13 | 25 | 11 | 40 |
| 78 | H | H | (CH$_2$)$_4$Ph | 11 | 55 | 17 | 105 |
| 66 | H | H | CH$_2$CH$_2$iPr | 12 | 26 | 12 | 39 |
| 72 | H | H | CH$_2$cyclohexyl | 9.7 | 27 | 9.0 | 40 |
| 76 | H | Et | CH$_2$CH$_2$-2-Pyr | 33 | 61 | 35 | 28 |
| 101 | H | H | CH$_2$cyclopropyl | 20 | 31 | 22 | 55 |
| 104 | H | H | CH(Me)CH$_2$iPr | 7.0 | 33 | 16 | 74 |
| 106 | H | Et | Pr | 21 | 30 | 20 | 60 |
| 107 | H | H | cyclohexyl | 13 | 39 | 28 | 110 |
| 108 | H | H | 1-Me—Bu | 9.0 | 35 | 15 | 80 |
| 112 | H | H | 6-Et-2-Pyr | 7.0 | 50 | 30 | 200 |
| 113 | H | iBu | iBu | 8.0 | 34 | 23 | 90 |
| 114 | H | H | cyclobutyl | 17 | 30 | 31 | 115 |
| 116 | H | allyl | cyclopentyl | 15 | 50 | 20 | 150 |
| 118 | H | Et | Bu | 13 | 40 | 15 | 60 |
| 120 | H | Et | isobutenyl | 17 | 24 | 17 | 42 |
| 125 | H | H | CH$_2$CF$_2$CF$_2$CF$_3$ | 14 | 37 | 24 | 39 |
| 128 | H | H | CH$_2$-3,5-(OMe)-4-Me-2-Pyridyl | 30 | 36 | 90 | 30 |
| 130 | H | H | CH$_2$-2-quinolinyl | 32 | 32 | 23 | 27 |
| 133 | H | H | CH(iPr)CO$_2$Et | 17 | 19 | 16 | 27 |
| 138 | H | CH$_2$Ph | CH$_2$CO$_2$Et | 31 | 31 | 15 | 16 |

All values are in nM.

Additional advantages, features and modifications will readily occur to those skilled in the art. Therefore, the invention in its broader aspects is not limited to the specific details and representative procedures, shown and described herein. Accordingly, various modifications may be made without departing from the spirit or scope of the general inventive concept as defined by the appended claims and their equivalents.

REFERENCES

1. Kodama, E., S. Shigeta, T. Sizuzki, E. De Clerq. 1996 Application of a gastric cancer cell line (MKN-28) for anti-adenovirus screening using the MTT method. Antiviral Res. 31:159-164.
2. Pauwels, R., J. Balzarini, M. Baba, R.Snoeck, D. Schols, P. Herdeweijn, J. Desmyter, E. De Clerq. 1988. Rapid and automated tetrazolium-based calorimetric assay for the detection of anti-HIV compounds. J. Virol. Methods. 20:309-321.
3. Yoshimura, K., R. Kato, M. F. Kavlick, A. Nguyen, V. Maroun, K. Maeda, K. A. Hussain, A. K. Ghosh, S. V. Gulnik, J. W. Erickson, H. Mitsuya. 2002. A potent HIV-1 protease inhibitor, UIC-94003(TMC-126), and selection of novel (A28S) mutation in the protease active site. J. Virol. 76:1349-1358.
4. Gulnik S V, Suvorov L I, Liu B, Yu B, Anderson B, Mitsuya H, Erickson J W. Kinetic characterization and cross-resistance patterns of HIV-1 protease mutants selected under drug pressure. Biochemistry. 1995, 34(29):9282-7.
5. Williams J W, Morrison J F. The kinetics of reversible tight-binding inhibition. Methods Enzymol. 1979; 63:437-67.

All of the references cited herein, including patents, patent applications, and publications, are hereby incorporated in their entireties by reference.

The claims below are not restricted to the particular embodiments described above.

What is claimed is:

1. A compound of the formula:

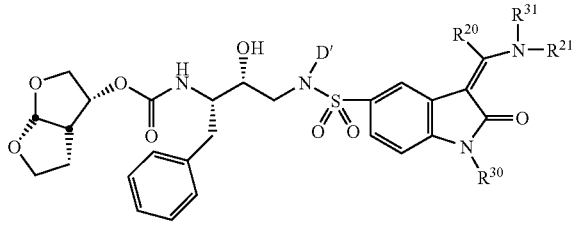

wherein:

D' is selected from the group consisting of alkyl, alkenyl, alkynyl, aryl, cycloalkyl and aralkyl, and is optionally substituted by alkyl, halo, nitro, cyano, CF$_3$, halo-C1-C6 alkyl, O-alkyl, or S-alkyl;

R20 is selected from the group consisting of H, alkyl, alkenyl and alkynyl;

R21 is H or is selected from the group consisting of alkyl, aryl, alkenyl, alkynyl, cycloalkyl, cycloalkenyl, heterocyclyl and heteroaryl, each optionally substituted by one or more halo, haloalkyl, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, aiylsulfonyl, cycloalkylsulfinyl, cycloalkylsulfonyl, heteroarylsulfinyl or heteroarylsulfonyl; or R21 and R31 together with the nitrogen atom to which they are attached, form a 3-8 membered unsubstituted or substituted heterocyclyl or heteroaryl ring; or R20 and R21 together form a 5-8 membered unsubstituted or substituted heterocyclyl or heteroaryl ring;

R31 is hydrogen, or is selected from the group consisting of alkyl, aryl, alkenyl, alkynyl, cycloalkyl, cycloalkenyl, heterocyclyl and heteroaryl, each optionally substituted by one or more halo, haloalkyl, hydroxy, hydroxyalkyl, R32, —COH, —COR32, —CO2H, —COOR32, —CONH2, —CONHR32, —CONR32R32, —OR32 OCOR32, —OCONHR32, OCONR32R32, cyano, nitro, amino, NHR32, NR32R32, NHCONH2, NHCONHR32, NHCONR32R32, NR32CONH2, NR32CONHR32, NR32CONR32R32, NHCOOR32, NR32COOR32, SR32, $SO_2NH_2$, $SO_2NHR32$, $SO_2NR32R32$, SOR32 or $SO_2R32$;

where each R32 is independently alkyl, aryl, alkenyl, alkynyl, cycloalkyl, cycloalkenyl, heterocyclyl and heteroaryl; and R30 is selected from the group consisting of hydrogen, OH and NHR, where R is H or is selected from the group consisting of alkyl, aryl, alkenyl, alkynyl, cycloalkyl, cycloalkenyl, heterocyclo and heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonarnido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl;

and the pharmaceutically acceptable salts thereof and stereoisomers thereof.

2. A compound selected from the group consisting of:

{1-Benzyl-3-[(3-dimethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-dimethylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-3-({3-[(ethyl-methyl-amino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-3-({3-[1-(ethyl-methyl-amino)-ethylidene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{3-[(methyl-propyl-amino)-methylene]-2-oxo-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{3-[1-(methyl-propyl-amino)-ethylidene]-2-oxo-2,3-dihydro-1H-indole-5-sulfonyl}-amino)-propyl]-carbamic acid hexahydro-furo[2,3-b]furan-3-yl ester;

{1-Benzyl-3-[(3-diethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-diethylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

{1-Benzyl-3-[(3-dipropylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-dipropylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

{1-Benzyl-2-hydroxy-3-[isobutyl-(2-oxo-3-piperidin-1-ylmethylene-2,3-dihydro-1H-indole-5-sulfonyl)-amino]-propyl}-carbamic acid hexahydro-furo[2,3-b]furan-3-yl ester;

(1-Benzyl-2-hydroxy-3-{isobutyl-[2-oxo-3-(1-piperidin-1-yl-ethylidene)-2,3-dihydro-1H-indole-5-sulfonyl]-amino}-propyl)-carbamic acid hexahydro-furo[2,3-b]furan-3-yl ester;

{1-Benzyl-2-hydroxy-3-[isobutyl-(2-oxo-3-piperazin-1-ylmethylene-2,3-dihydro-1H-indole-5-sulfonyl)-amino]-propyl}-carbamic acid hexahydro-furo[2,3-b]furan-3-yl ester;

{1-Benzyl-2-hydroxy-3-[isobutyl-(3-morpholin-4-ylmethylene-2-oxo-2,3-dihydro-1H-indole-5-sulfonyl)-amino]-propyl}-carbamic acid hexahydro-furo[2,3-b]furan-3-yl ester;

{3-[(3-Aminomethylene-2-oxo-2,3-dihydro-1H-indole-5-sulfonyl)-isobutyl-amino]-1-benzyl-2-hydroxy-propyl}-carbamic acid hexahydro-furo[2,3-b]furan-3-yl ester;

(3-{[3-(1-Amino-ethylidene)-2-oxo-2,3-dihydro-1H-indole-5-sulfonyl]-isobutyl-amino}-1-benzyl-2-hydroxypropyl)-carbamic acid hexahydro-furo[2,3-b]furan-3-yl ester;

{1-Benzyl-2-hydroxy-3-[isobutyl-(3-methylaminomethylene-2-oxo-2,3-dihydro-1H-indole-5-sulfonyl)-amino]-propyl}-carbamic acid hexahydro-furo[2,3-b]furan-3-yl ester;

(1-Benzyl-2-hydroxy-3-{isobutyl-[3-(1-methylamino-ethylidene)-2-oxo-2,3-dihydro-1H-indole-5-sulfonyl]-amino}-propyl)-carbamic acid hexahydro-furo[2,3-b]furan-3-yl ester;

{1-Benzyl-3-[(3-ethylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-ethylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-2-hydroxy-3-(isobutyl-{2-oxo-3-[(2,2,2-trifluoro-ethylamino)-methylene]-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{2-oxo-3-[1-(2,2,2-trifluoro-ethylamino)-ethylidene]-2,3-dihydro-1H-indole-5-sulfonyl}-amino)-propyl]-carbamic acid hexahydro-furo[2,3-b]furan-3-yl ester;

[1-Benzyl-2-hydroxy-3-({3-[(2-hydroxy-ethylamino)-methylene]-2-oxo-2,3-dihydro-1H-indole-5-sulfonyl}-isobutyl-amino)-propyl]-carbamic acid hexahydro-furo[2,3-b]furan-3-yl ester;

[1-Benzyl-2-hydroxy-3-({3-[1-(2-hydroxy-ethylamino)-ethylidene]-2-oxo-2,3-dihydro-1H-indole-5-sulfonyl}-isobutyl-amino)-propyl]-carbamic acid hexahydro-furo[2,3-b]furan-3-yl ester;

[1-Benzyl-2-hydroxy-3-(isobutyl-{3-[(2-methoxy-ethylamino)-methylene]-2-oxo-2,3-dihydro-1H-indole-5-sulfonyl}-amino)-propyl]-carbamic acid hexahydro-furo [2,3-b]furan-3-yl ester;

[1-Benzyl-2-hydroxy-3-(isobutyl-{3-[1-(2-methoxy-ethylamino)-ethylidene]-2-oxo-2,3-dihydro-1H-indole-5-sulfonyl}-amino)-propyl]-carbamic acid hexahydro-furo[2,3-b]furan-3-yl ester;

[1-Benzyl-3-({3-[(2-dimethylamino-ethylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-3-({3-[1-(2-dimethylamino-ethylamino)-ethylidene]-2-oxo-2,3-dihydro-1H-indole-5-sulfonyl}-isobutyl-amino)-2-hydroxy-propyl]-carbamic acid hexahydro-furo[2,3-b]furan-3-yl ester;

(1-Benzyl-2-hydroxy-3-{isobutyl-[3-(isopropylamino-methylene)-2-oxo-2,3-dihydro-1H-indole-5-sulfonyl]-amino}-propyl)-carbamic acid hexahydro-furo[2,3-b]furan-3-yl ester;

(1-Benzyl-2-hydroxy-3-{isobutyl-[3-(1-isopropylamino-ethylidene)-2-oxo-2,3-dihydro-1H-indole-5-sulfonyl]-amino}-propyl)-carbamic acid hexahydro-furo[2,3-b]furan-3-yl ester;

{1-Benzyl-2-hydroxy-3-[isobutyl-(2-oxo-3-propylaminomethylene-2,3-dihydro-1H-indole-5-sulfonyl)-amino]-propyl}-carbamic acid hexahydro-furo[2,3-b]furan-3-yl ester;

(1-Benzyl-2-hydroxy-3-{isobutyl-[2-oxo-3-(1-propylamino-ethylidene)-2,3-dihydro-1H-indole-5-sulfonyl]-amino}-propyl)-carbamic acid hexahydro-furo[2,3-b]furan-3-yl ester;

{1-Benzyl-2-hydroxy-3-[isobutyl-(2-oxo-3-pyrrolidin-2-ylidene-2,3-dihydro-1H-indole-5-sulfonyl)-amino]-propyl}-carbamic acid hexahydro-furo[2,3-b]furan-3-yl ester;

{1-Benzyl-3-[(3-butylaminomethylene-2-oxo-2,3-dihydro-1H-indole-5-sulfonyl)-isobutyl-amino]-2-hydroxy-propyl}-carbamic acid hexahydro-furo[2,3-b]furan-3-yl ester;

(1-Benzyl-3-{[3-(1-butylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

(1-Benzyl-2-hydroxy-3-{isobutyl-[3-(isobutylamino-methylene)-2-oxo-2,3-dihydro-1H-indole-5-sulfonyl]-amino}-propyl)-carbamic acid hexahydro-furo[2,3-b]furan-3-yl ester;

(1-Benzyl-2-hydroxy-3-{isobutyl-[3-(1-isobutylamino-ethylidene)-2-oxo-2,3-dihydro-1H-indole-5-sulfonyl]-amino}-propyl)-carbamic acid hexahydro-furo[2,3-b]furan-3-yl ester;

(1-Benzyl-3-{[3-(tert-butylamino-methylene)-2-oxo-2,3-dihydro-1H-indole-5-sulfonyl]-isobutyl-amino}-2-hydroxy-propyl)-carbamic acid hexahydro-furo[2,3-b]furan-3-yl ester;

(1-Benzyl-3-{[3-(1-tert-butylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-3-({3-[(2,2-dimethyl-propylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-3-({3-[1-(2,2-dimethyl-propylamino)-ethylidene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{3-[(2-methyl-butylamino)-methylene]-2-oxo-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{3-[(3-methyl-butylamino)-methylene]-2-oxo-2,3-dihydro-1H-indole-5-sulfonyl}-amino)-propyl]-carbamic acid hexahydro-furo[2,3-b]furan-3-yl ester;

[1-Benzyl-3-({3-[(3,3-dimethyl-butylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{3-[(1-isopropyl-2-methyl-propylamino)-methylene]-2-oxo-2,3-dihydro-1H-indole-5-sulfonyl}-amino)-propyl]-carbamic acid hexahydro-furo[2,3-b]furan-3-yl ester;

{1-Benzyl-2-hydroxy-3-[isobutyl-(2-oxo-3-phenylaminomethylene-2,3-dihydro-1H-indole-5-sulfonyl)-amino]-propyl}-carbamic acid hexahydro-furo[2,3-b]furan-3-yl ester;

(1-Benzyl-3-{[3-(benzylamino-methylene)-2-oxo-2,3-dihydro-1H-indole-5-sulfonyl]-isobutyl-amino}-2-hydroxy-propyl)-carbamic acid hexahydro-furo[2,3-b]furan-3-yl ester;

(1-Benzyl-3-{[3-(1-benzylamino-ethylidene)-2-oxo-2,3-dihydro-1H-indole-5-sulfonyl]-isobutyl-amino}-2-hydroxy-propyl)-carbamic acid hexahydro-furo[2,3-b]furan-3-yl ester;

[1-Benzyl-3-({3-[(cyclohexylmethyl-amino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

{1-Benzyl-2-hydroxy-3-[isobutyl-(2-oxo-3-{[(pyridin-4-ylmethyl)-amino]-methylene}-2,3-dihydro-1H-indole-5-sulfonyl)-amino]-propyl}-carbamic acid hexahydro-furo[2,3-b]furan-3-yl ester;

(1-Benzyl-2-hydroxy-3-{isobutyl-[2-oxo-3-(phenethylamino-methylene)-2,3-dihydro-1H-indole-5-sulfonyl]-amino}-propyl)-carbamic acid hexahydro-furo[2,3-b]furan-3-yl ester;

[1-Benzyl-3-({3-[(2-cyclohex-1-enyl-ethylamino)-methylene]-2-oxo-2,3-dihydro-1H-indole-5-sulfonyl}-isobutyl-amino)-2-hydroxy-propyl]-carbamic acid hexahydro-furo[2,3-b]furan-3-yl ester;

[1-Benzyl-2-hydroxy-3-(isobutyl-{2-oxo-3-[(2-pyridin-2-yl-ethylamino)-methylene]-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{2-oxo-3-[(2-phenyl-propylamino)-methylene]-2,3-dihydro-1H-indole-5-sulfonyl}-amino)-propyl]-carbamic acid hexahydro-furo[2,3-b]furan-3-yl ester;

[1-Benzyl-2-hydroxy-3-(isobutyl-{2-oxo-3-[(4-phenyl-butylamino)-methylene]-2,3-dihydro-1H-indole-5-sulfonyl}-amino)-propyl]-carbamic acid hexahydro-furo[2,3-b]furan-3-yl ester;

{1-Benzyl-2-hydroxy-3-[isobutyl-(3-nonylaminomethyl-ene-2-oxo-2,3-dihydro-1H-indole-5-sulfonyl)-amino]-propyl}-carbamic acid hexahydro-furo[2,3-b]furan-3-yl ester; and (1-Benzyl-2-hydroxy-3-{[3-(1-hydroxy-ethylidene)-2-oxo-2,3-dihydro-1H-indole-5-sulfonyl]-isobutyl-amino}-propyl)-carbamic acid hexahydro-furo[2,3-b]furan-3-yl ester and the pharmaceutically acceptable salts thereof, as single stereoisomers or mixtures of stereoisomers.

3. A compound that is shown in the table:

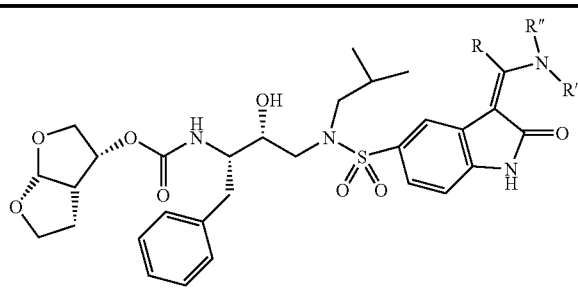

| Compound | R | R' | R'' |
|---|---|---|---|
| 21 | H | Me | Me |
| 25 | Me | Me | Me |
| 26 | H | Me | Et |
| 27 | Me | Me | Et |
| 28 | H | Me | Pr |
| 29 | Me | Me | Pr |
| 30 | H | Et | Et |
| 31 | Me | Et | Et |
| 32 | H | Pr | Pr |
| 33 | Me | Pr | Pr |
| 34 | H | | CH2CH2CH2CH2CH2 |
| 35 | Me | | CH2CH2CH2CH2CH2 |
| 36 | H | | CH2CH2NHCH2CH2 |
| 37 | H | | CH2CH2OCH2CH2 |
| 38 | H | H | H |
| 39 | Me | H | H |
| 40 | H | H | Me |
| 41 | Me | H | Me |
| 42 | H | H | Et |
| 43 | Me | H | Et |
| 44 | H | H | $CH_2CF_3$ |
| 45 | Me | H | $CH_2CF_3$ |
| 46 | H | H | $CH_2CH_2OH$ |
| 47 | Me | H | $CH_2CH_2OH$ |
| 48 | H | H | $CH_2CH_2OMe$ |
| 49 | Me | H | $CH_2CH_2OMe$ |
| 50 | H | H | $CH_2CH_2NMe_2$ |
| 51 | Me | H | $CH_2CH_2NMe_2$ |
| 52 | H | H | iPr |
| 53 | Me | H | iPr |
| 54 | H | H | Pr |
| 55 | Me | H | Pr |
| 56 | —$CH_2CH_2$— | H | —$CH_2$ linked to R |
| 57 | H | H | Bu |
| 59 | Me | H | Bu |
| 60 | H | H | iBu |
| 61 | Me | H | iBu |
| 62 | H | H | tBu |
| 63 | Me | H | tBu |
| 22 | H | H | $CH_2tBu$ |
| 64 | Me | H | $CH_2tBu$ |
| 65 | H | H | 2-Me-Bu |
| 66 | H | H | $CH_2CH_2$i-Pr |
| 67 | H | H | $CH_2CH_2tBu$ |
| 68 | H | H | $CH(iPr)_2$ |
| 69 | H | H | Ph |
| 70 | H | H | $CH_2Ph$ |

-continued

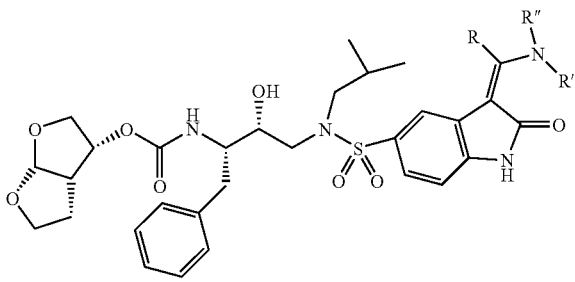

| Compound | R | R' | R" |
|---|---|---|---|
| 71 | Me | H | CH$_2$Ph |
| 72 | H | H | CH$_2$C$_6$H$_{11}$ |
| 73 | H | H | CH$_2$-4-Pyr |
| 74 | H | H | (CH$_2$)$_2$Ph |
| 75 | H | H | CH$_2$CH$_2$C$_6$H$_{10}$ |
| 76 | H | H | (CH$_2$)$_2$-2-Pyr |
| 77 | H | H | CH$_2$CH(Me)Ph |
| 78 | H | H | (CH$_2$)$_4$Ph |
| 79 | H | H | (CH$_2$)$_8$CH$_3$ |
| 81 | H | H | (CH2)2OPh |
| 82 | H | H | 2-CH2CH2NMe-pyrollidine |
| 83 | Me | H | (CH2)2-2-Pyridyl |
| 84 | H | Et | CH2-4-Pyridyl |
| 85 | H | CH2-2-Pyridyl | CH2-2-Pyridyl |
| 86 | H | Et | CH2-2-Pyridyl |
| 87 | H | H | (CH2)2-3-Pyridyl |
| 88 | H | H | (CH2)5 linked to R |
| 89 | H | H | (CH2)3OEt |
| 90 | H | H | (CH2)2-4-Pyridyl |
| 91 | H | Me | (CH2)2-2-Pyridyl |
| 92 | H | H | (CH2)6OH |
| 93 | H | C6H11 | CH2-2-Pyridyl |
| 94 | H | H | (CH2)2SEt |
| 95 |  | H | (CH2)4 linked to R |
| 96 | H | H | CH2CH2-4-morpholinyl |
| 97 | H | H | s-Bu |
| 98 | H | H | CH(Me)iPr |
| 99 | H | CH2CH2CH2 | CH(CO2Et)CH2 linked to R' |
| 100 | H | H | CH(Et)2 |
| 101 | H | H | CH2cyclopropyl |
| 102 | H | Me | cyclohexyl |
| 103 | H | H | CH2CH(Et)2 |
| 104 | H | H | CH(Me)CH2iPr |
| 105 | H | H | CH(Me)(CH2)2iPr |
| 106 | H | Et | Pr |
| 107 | H | H | cyclohexyl |
| 108 | H | H | 1-Me-Bu |
| 109 | H | Me | Bu |
| 110 | H | H | cyclopentyl |
| 111 | H | Me | iBu |
| 112 | H | H | 6-Et-2-Pyridyl |
| 113 | H | iBu | iBu |
| 114 | H | H | cyclobutyl |
| 115 | H | Et | iPr |
| 116 | H | allyl | cyclopentyl |
| 117 | H | H | CH2CH2NHCO2tBu |
| 118 | H | Et | Bu |
| 119 | H | H | CH2CF2CF3 |
| 120 | H | Et | isobutenyl |
| 121 | H | H | CH2CH2NHPh |
| 122 | H | Pr | 2-Bu |
| 123 | H | H | CH2-2-benzimidazolyl |
| 124 | H | H | CH2-2-(5-Me-Pyrazinyl) |
| 125 | H | H | CH2CF2CF2CF3 |
| 126 | H | H | (CH2)2-4-NH2Ph |
| 127 | H | H | (CH2)2-4-OHPh |
| 128 | H | H | CH2-3,5-(OMe)-4Me-2-Pyridyl |
| 129 | H | H | CH2-(2-Me-4-thiazolyl) |
| 130 | H | H | CH2-2-quinolinyl |
| 131 | Me | H | CH2cyclohexyl |
| 132 | H | H | CH2CO2tBu |
| 133 | H | H | CH(iPr)CO2Et |
| 134 | H | H | CH(CH2Ph)CO2Me |

-continued

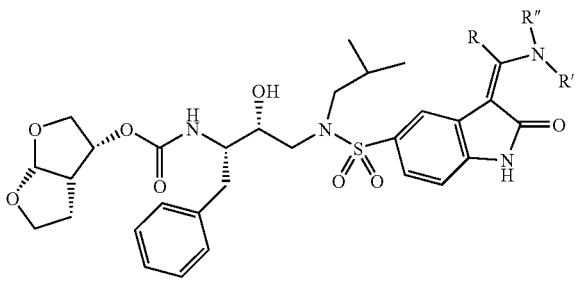

| Compound | R | R' | R" |
|---|---|---|---|
| 135 | H | H | CH(CH2-4-ClPh)CO2Et |
| 136 | H | H | CH2CO2CH2Ph |
| 137 | H | H | (CH2)2CO2CH2Ph |
| 138 | H | CH2Ph | CH2CO2Et |
| 139 | H | | CH2CH(CO2Me)CH2 linked to R' |
| 140 | H | H | CO2Et(NCO2Et) |
| 141 | H | H | CO2Et |
| 142 | H | H | Ac |
| 143 | H | H | Cyclopropyl |
| 144 | H | H | CH2-5-benzofuranyl. |

4. The compound of claim 1, wherein the compound is present as a single stereoisomer.

5. A pharmaceutical composition comprising, as an active ingredient, the compound of claim 1.

6. The pharmaceutical composition of claim 5, wherein the composition is a solid formulation adapted for oral administration.

7. The pharmaceutical composition of claim 5, wherein the composition is a liquid formulation adapted for oral or parenteral administration.

8. A pharmaceutical composition comprising the compound of claim 1, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, and intrathecally.

9. The compound of claim 5 bound in a complex with wild type or a drug resistant mutant form of HIV-1 protease 10. A pharmaceutical composition, comprising the compound of claim 1 and another agent selected from the group consisting of an antiretroviral agent, an HIV inhibitor, an HIV protease inhibitor and an HIV reverse transcriptase inhibitor.

11. A method of treating a patient suffering from HIV infection, comprising administering to said patient the compound of claim 1.

12. A method of treating a patient suffering from HIV infection, comprising administering to said patient a composition of claim 10.

13. The method of claim 12, wherein said patient is suffering from a multi-drug resistant HIV infection.

14. A method of inhibiting an HIV protease, comprising contacting the HIV protease with the compound of claim 1.

15. A method of inhibiting an HIV protease, comprising contacting the HIV protease with a composition of claim 9.

16. The method of claim 15, further comprising administering a cytochrome P450 inhibitor.

17. The compound of claim 1, wherein the compound is present as a mixture of stereoisomers.

* * * * *